(12) United States Patent
De Berardinis et al.

(10) Patent No.: US 11,744,901 B2
(45) Date of Patent: Sep. 5, 2023

(54) PHAGE CONJUGATES AND USES THEREOF

(71) Applicant: CONSIGLIO NAZIONALE DELLE RICERCHE, Pomezia (IT)

(72) Inventors: Piergiuseppe De Berardinis, Rome (IT); Rossella Sartorius, Rome (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 533 days.

(21) Appl. No.: 16/478,338

(22) PCT Filed: Jan. 29, 2018

(86) PCT No.: PCT/IB2018/050525
§ 371 (c)(1),
(2) Date: Jul. 16, 2019

(87) PCT Pub. No.: WO2018/138696
PCT Pub. Date: Aug. 2, 2018

(65) Prior Publication Data
US 2019/0343965 A1  Nov. 14, 2019

(30) Foreign Application Priority Data
Jan. 27, 2017 (IT) .................. 102017000009270

(51) Int. Cl.
| | |
|---|---|
| *A61K 47/69* | (2017.01) |
| *A61P 35/00* | (2006.01) |
| *A61K 39/39* | (2006.01) |
| *C07K 14/52* | (2006.01) |
| *C07K 14/77* | (2006.01) |
| *C07K 16/28* | (2006.01) |
| *C12N 7/00* | (2006.01) |
| *A61K 39/00* | (2006.01) |

(52) U.S. Cl.
CPC .......... *A61K 47/6901* (2017.08); *A61K 39/39* (2013.01); *A61P 35/00* (2018.01); *C07K 14/521* (2013.01); *C07K 14/77* (2013.01); *C07K 16/2851* (2013.01); *C12N 7/00* (2013.01); *A61K 2039/55572* (2013.01); *A61K 2039/585* (2013.01); *C07K 2317/622* (2013.01); *C07K 2317/77* (2013.01); *C07K 2319/33* (2013.01); *C07K 2319/42* (2013.01); *C07K 2319/735* (2013.01); *C07K 2319/74* (2013.01); *C12N 2795/14122* (2013.01); *C12N 2795/14132* (2013.01); *C12N 2795/14145* (2013.01)

(58) Field of Classification Search
None
See application file for complete search history.

(56) References Cited

FOREIGN PATENT DOCUMENTS

| WO | 2008/109398 A1 | 9/2008 |
|---|---|---|
| WO | WO2013/138716 | * 9/2013 |

OTHER PUBLICATIONS

Sartorius et al (EMBO Molecular Medicine, 7(7):973-988, Apr. 17, 2015).*
Sartorius et al (Eur. J. Immunology 41:2573-2584, 2011).*
Gableh et al (Journal of Biomedical Science 23(16):1-11, 2016).*
Dong et al (Biochem J, 473:7-19, 2016).*
Ghinnagow et al (Frontiers in Immunology, 8: Article 879, published Jul. 27, 2017).*
Macho-Fernandez et al. (Journal of Immunology, 193:961-969, 2014).*
Sara J. McKee; et al., "Virus-like particles and a-galactosylceramide form a self-adjuvanting composite particle that elicits anti-tumor responses", Journal of Controlled Release, vol. 159, No. 3., 2012, pp. 338-345.
Rossella Sartorius; et al., "Vaccination with filamentous bacteriophages targeting DEC-205 induces DC maturation and potent anti-tumor T-cell responses in the absence of adjuvants", European Journal of Immunology, vol. 41, No. 9, 2011, pp. 2573-2584.
Dina Mascolo; et al., "Phage display of a CTL epitope elicits a long-term in vivo cytotoxic response", FEMS Immunology and Medical Microbiology, vol. 50, No. 1, 2007, pp. 59-66.
ISA/EP, PCT International Search Report issued in connection with PCT International Application No. PCT/IB2018/050525, dated May 18, 2018 (5 pages).

* cited by examiner

*Primary Examiner* — Oluwatosin A Ogunbiyi
(74) *Attorney, Agent, or Firm* — Lucas & Mercanti, LLP

(57) ABSTRACT

The present invention relates to pharmaceutical compositions containing lipid-bacteriophage conjugates, wherein the bacteriophage:lipid ratio is in the range of 3:1 to 100:1 and wherein the lipid is an immunologically active lipid and the bacteriophage is a filamentous bacteriophage, and uses thereof. Preferably, the bacteriophage is engineered to stimulate an immune response and/or bind to a target cell.

16 Claims, 5 Drawing Sheets
Specification includes a Sequence Listing.

A

B

SEQUENCE LISTING

```
<160> NUMBER OF SEQ ID NOS: 19

<210> SEQ ID NO 1
<211> LENGTH: 8
<212> TYPE: PRT
<213> ORGANISM: Artificial Sequence
<220> FEATURE:
<223> OTHER INFORMATION: synthetic

<400> SEQUENCE: 1

Ser Ile Ile Asn Phe Glu Lys Leu
1               5

<210> SEQ ID NO 2
<211> LENGTH: 357
<212> TYPE: DNA
<213> ORGANISM: Artificial Sequence
<220> FEATURE:
<223> OTHER INFORMATION: synthetic

<400> SEQUENCE: 2
gcggctcaac cggcgatggc cgattacaag caagcggtgg taacccagga atccgcactg      60
acgacctcgc caggggaaac cgtgacactg acttgtcgct cgtctacagg agccgttacc     120
atttccaact atgccaattg ggtacaggag aaaccggacc atctgtttac gggcttaatt     180
```

-continued

```
ggcgggatca acaatcgcgc tcctggcgtt ccagcgcgtt ttagcggtag cttgattggc    240
gataaagccg ctcttaccat tactggtgca cagaccgagg atgaagccat ctactttgc     300 gcactgtggt ataacaacca gtttatcttc ggtagcggca ccaaagtcac ggtcttg       357
```

<210> SEQ ID NO 3
<211> LENGTH: 119
<212> TYPE: PRT
<213> ORGANISM: Artificial Sequence
<220> FEATURE:
<223> OTHER INFORMATION: synthetic

<400> SEQUENCE: 3

```
Ala Ala Gln Pro Ala Met Ala Asp Tyr Lys Gln Ala Val Val Thr Gln
1               5                   10                  15

Glu Ser Ala Leu Thr Thr Ser Pro Gly Glu Thr Val Thr Leu Thr Cys
            20                  25                  30

Arg Ser Ser Thr Gly Ala Val Thr Ile Ser Asn Tyr Ala Asn Trp Val
        35                  40                  45

Gln Glu Lys Pro Asp His Leu Phe Thr Gly Leu Ile Gly Gly Ile Asn
    50                  55                  60

Asn Arg Ala Pro Gly Val Pro Ala Arg Phe Ser Gly Ser Leu Ile Gly
65                  70                  75                  80

Asp Lys Ala Ala Leu Thr Ile Thr Gly Ala Gln Thr Glu Asp Glu Ala
                85                  90                  95

Ile Tyr Phe Cys Ala Leu Trp Tyr Asn Asn Gln Phe Ile Phe Gly Ser
            100                 105                 110

Gly Thr Lys Val Thr Val Leu
        115
```

<210> SEQ ID NO 4
<211> LENGTH: 366
<212> TYPE: DNA
<213> ORGANISM: Artificial Sequence
<220> FEATURE:
<223> OTHER INFORMATION: synthetic

<400> SEQUENCE: 4

```
gaagtccagt tacagcaaag tggcccggtt ctggtgaaac cgggagcgag tgtgaagatg    60
tcgtgcaaag cctctggaaa cacctttact gactcgttta tgcactggat gaaacagtcg    120
catggcaaat cactggaatg gattggtatc atcaacccgt acaatggcgg gacctcttac    180
aaccagaagt tcaagggcaa agcgaccctg actgtggata atccagcag cacggcgtat     240 atggagctca acagcctgac cagtgaggat agcgccgtat attattgcgc tcgcaatggg    300
gtacgctact atttcgacta ttggggccag ggtacgacgt gaccgtttc atctgcctca     360 ggggcg                                                              366
```

<210> SEQ ID NO 5
<211> LENGTH: 122
<212> TYPE: PRT
<213> ORGANISM: Artificial Sequence
<220> FEATURE:
<223> OTHER INFORMATION: synthetic

<400> SEQUENCE: 5

```
Glu Val Gln Leu Gln Gln Ser Gly Pro Val Leu Val Lys Pro Gly Ala
1               5                   10                  15

Ser Val Lys Met Ser Cys Lys Ala Ser Gly Asn Thr Phe Thr Asp Ser
            20                  25                  30
```

Phe Met His Trp Met Lys Gln Ser His Gly Lys Ser Leu Glu Trp Ile
         35                  40                  45

Gly Ile Ile Asn Pro Tyr Asn Gly Gly Thr Ser Tyr Asn Gln Lys Phe
     50                  55                  60

Lys Gly Lys Ala Thr Leu Thr Val Asp Lys Ser Ser Thr Ala Tyr
65                  70                  75                  80

Met Glu Leu Asn Ser Leu Thr Ser Glu Asp Ser Ala Val Tyr Tyr Cys
                 85                  90                  95

Ala Arg Asn Gly Val Arg Tyr Tyr Phe Asp Tyr Trp Gly Gln Gly Thr
            100                 105                 110

Thr Leu Thr Val Ser Ser Ala Ser Gly Ala
        115                 120

<210> SEQ ID NO 6
<211> LENGTH: 63
<212> TYPE: DNA
<213> ORGANISM: Artificial Sequence
<220> FEATURE:
<223> OTHER INFORMATION: synthetic

<400> SEQUENCE: 6
ggtggaggcg gtggtagtgg cggcggtggg tccggcggtg gcggtagtgg cggtggtggt      60
tct                                                                   63

<210> SEQ ID NO 7
<211> LENGTH: 21
<212> TYPE: PRT
<213> ORGANISM: Artificial Sequence
<220> FEATURE:
<223> OTHER INFORMATION: synthetic

<400> SEQUENCE: 7

Gly Gly Gly Gly Gly Ser Gly Gly Gly Ser Gly Gly Gly Gly Ser
1               5                  10                  15

Gly Gly Gly Gly Ser
            20

<210> SEQ ID NO 8
<211> LENGTH: 36
<212> TYPE: DNA
<213> ORGANISM: Artificial Sequence
<220> FEATURE:
<223> OTHER INFORMATION: synthetic

<400> SEQUENCE: 8
acctccggtt acccgtacga cgttccggac tacgct                               36

<210> SEQ ID NO 9
<211> LENGTH: 12
<212> TYPE: PRT
<213> ORGANISM: Artificial Sequence
<220> FEATURE:
<223> OTHER INFORMATION: synthetic

<400> SEQUENCE: 9

Thr Ser Gly Tyr Pro Tyr Asp Val Pro Asp Tyr Ala
1               5                   10

<210> SEQ ID NO 10
<211> LENGTH: 27
<212> TYPE: DNA
<213> ORGANISM: Artificial Sequence
<220> FEATURE:
<223> OTHER INFORMATION: synthetic

<400> SEQUENCE: 10
ggtggtggtg gttctggtgg tggtggt                                        27

<210> SEQ ID NO 11
<211> LENGTH: 9
<212> TYPE: PRT
<213> ORGANISM: Artificial Sequence
<220> FEATURE:
<223> OTHER INFORMATION: synthetic

<400> SEQUENCE: 11

Gly Gly Gly Gly Ser Gly Gly Gly Gly
1               5

<210> SEQ ID NO 12
<211> LENGTH: 1275
<212> TYPE: DNA
<213> ORGANISM: Artificial Sequence
<220> FEATURE:
<223> OTHER INFORMATION: synthetic

<400> SEQUENCE: 12
gtgaaaaaat tattattcgc aattccttta gttgttcctt tctattctca ctcgagtgaa      60
actgttacta gttgtttagc aaaacctcat acagaaaatt catttactaa cgtctggaaa     120
gacgacaaaa ctttagatcg ttacgctaac tatgagggct gtctgtggaa tgctacaggc     180
gttgtggttt gtactggtga cgaaactcag tgttacggta catgggttcc tattgggctt     240
gctatccctg aaaatgaggg tggtggctct gagggtggcg ttctgaggg tggcggttct      300 gagggtggcg gtactaaacc tcctgagtac ggtgatacac ctattccggg ctatacttat     360
atcaaccctc tcgacggcac ttatccgcct ggtactgagc aaaaccccgc taatcctaat     420
ccttctcttg aggagtctca gcctcttaat actttcatgt ttcagaataa taggttccga     480
aataggcagg gtgcattaac tgtttatacg ggcactgtta ctcaaggcac tgaccccgtt     540
aaaacttatt accagtacac tcctgtatca tcaaaagcca tgtatgacgc ttactggaac     600
ggtaaattca gagactgcgc tttccattct ggctttaatg aggatccatt cgtttgtgaa     660
tatcaaggcc aatcgtctga cctgcctcaa cctcctgtca atgctggcgg cggctctggt     720
ggtggttctg gtggcggctc tgagggtggc ggctctgagg gtggcggttc tgagggtggc     780
ggctctgagg gtggcggttc cggtggcggc tccggttccg gtgattttga ttatgaaaaa     840
atggcaaacg ctaataaggg ggctatgacc gaaaatgccg atgaaaacgc gctacagtct     900
gacgctaaag gcaaacttga ttctgtcgct actgattacg gtgctgctat cgatggtttc     960
attggtgacg tttccggcct tgctaatggt aatggtgcta ctggtgattt tgctggctct    1020
aattcccaaa tggctcaagt cggtgacggt gataattcac tttaatgaa taatttccgt    1080 caatatttac cttctttgcc tcagtcggtt gaatgtcgcc cttatgtctt tggcgctggt    1140
aaaccatatg aattttctat tgattgtgac aaaataaact tattccgtgg tgtctttgcg    1200
tttcttttat atgttgccac ctttatgtat gtattttcga cgtttgctaa catactgcgt    1260
aataaggagt cttaa                                                    1275

<210> SEQ ID NO 13
<211> LENGTH: 424
<212> TYPE: PRT
<213> ORGANISM: Artificial Sequence
<220> FEATURE:
<223> OTHER INFORMATION: synthetic

<400> SEQUENCE: 13

```
Val Lys Lys Leu Leu Phe Ala Ile Pro Leu Val Pro Phe Tyr Ser
1               5                   10                  15

His Ser Ser Glu Thr Val Thr Ser Cys Leu Ala Lys Pro His Thr Glu
            20                  25                  30

Asn Ser Phe Thr Asn Val Trp Lys Asp Asp Lys Thr Leu Asp Arg Tyr
        35                  40                  45

Ala Asn Tyr Glu Gly Cys Leu Trp Asn Ala Thr Gly Val Val Cys
    50                  55                  60

Thr Gly Asp Glu Thr Gln Cys Tyr Gly Thr Trp Val Pro Ile Gly Leu
65              70                  75                  80

Ala Ile Pro Glu Asn Glu Gly Gly Ser Glu Gly Gly Ser Glu
            85                  90                  95

Gly Gly Gly Ser Glu Gly Gly Thr Lys Pro Pro Glu Tyr Gly Asp
            100                 105                 110

Thr Pro Ile Pro Gly Tyr Thr Tyr Ile Asn Pro Leu Asp Gly Thr Tyr
            115                 120                 125

Pro Pro Gly Thr Glu Gln Asn Pro Ala Asn Pro Asn Pro Ser Leu Glu
130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
                180                 185                 190

Ala Met Tyr Asp Ala Tyr Trp Asn Gly Lys Phe Arg Asp Cys Ala Phe
                195                 200                 205

His Ser Gly Phe Asn Glu Asp Pro Phe Val Cys Glu Tyr Gln Gly Gln
            210                 215                 220

Ser Ser Asp Leu Pro Gln Pro Pro Val Asn Ala Gly Gly Ser Gly
225                 230                 235                 240

Gly Gly Ser Gly Gly Gly Ser Glu Gly Gly Ser Glu Gly Gly
            245                 250                 255

Ser Glu Gly Gly Ser Glu Gly Gly Ser Gly Gly Ser Gly
            260                 265                 270

Ser Gly Asp Phe Asp Tyr Glu Lys Met Ala Asn Ala Asn Lys Gly Ala
            275                 280                 285

Met Thr Glu Asn Ala Asp Glu Asn Ala Leu Gln Ser Asp Ala Lys Gly
            290                 295                 300

Lys Leu Asp Ser Val Ala Thr Asp Tyr Gly Ala Ala Ile Asp Gly Phe
305                 310                 315                 320

Ile Gly Asp Val Ser Gly Leu Ala Asn Gly Asn Gly Ala Thr Gly Asp
            325                 330                 335

Phe Ala Gly Ser Asn Ser Gln Met Ala Gln Val Gly Asp Gly Asp Asn
            340                 345                 350

Ser Pro Leu Met Asn Asn Phe Arg Gln Tyr Leu Pro Ser Leu Pro Gln
            355                 360                 365

Ser Val Glu Cys Arg Pro Tyr Val Phe Gly Ala Gly Lys Pro Tyr Glu
            370                 375                 380

Phe Ser Ile Asp Cys Asp Lys Ile Asn Leu Phe Arg Gly Val Phe Ala
385                 390                 395                 400
```

Phe Leu Leu Tyr Val Ala Thr Phe Met Tyr Val Ser Thr Phe Ala
            405                 410                 415

Asn Ile Leu Arg Asn Lys Glu Ser
            420

<210> SEQ ID NO 14
<211> LENGTH: 1320
<212> TYPE: DNA
<213> ORGANISM: Artificial Sequence
<220> FEATURE:
<223> OTHER INFORMATION: synthetic

<400> SEQUENCE: 14

| | | | | |
|---|---|---|---|---|
| gtgaaaaaat | tattattcgc | aattccttta | gttgttcctt | tctattctca ctcgagtgaa | 60 |
| actgttacta | gtggtacctc | cggttacccg | tacgacgttc | cggactacgc tactagttgt | 120 |
| ttagcaaaac | ctcatacaga | aaattcattt | actaacgtct | ggaaagacga caaaacttta | 180 |
| gatcgttacg | ctaactatga | gggctgtctg | tggaatgcta | caggcgttgt ggtttgtact | 240 |
| ggtgacgaaa | ctcagtgtta | cggtacatgg | gttcctattg | gcttgctat ccctgaaaat | 300 |
| gagggtggtg | gctctgaggg | tggcggttct | gagggtggcg | gttctgaggg tggcggtact | 360 |
| aaacctcctg | agtacggtga | tacacctatt | ccgggctata | cttatatcaa ccctctcgac | 420 |
| ggcacttatc | cgcctggtac | tgagcaaaac | cccgctaatc | ctaatccttc tcttgaggag | 480 |
| tctcagcctc | ttaatacttt | catgtttcag | aataataggt | tccgaaatag caggggtgca | 540 |
| ttaactgttt | atacgggcac | tgttactcaa | ggcactgacc | ccgttaaaac ttattaccag | 600 |
| tacactcctg | tatcatcaaa | agccatgtat | gacgcttact | ggaacggtaa attcagagac | 660 |
| tgcgctttcc | attctggctt | taatgaggat | ccattcgttt | gtgaatatca aggccaatcg | 720 |
| tctgacctgc | tcaacctcc | tgtcaatgct | ggcggcggct | ctggtggtgg ttctggtggc | 780 |
| ggctctgagg | gtggcggctc | tgagggtggc | ggttctgagg | gtggcggctc tgagggtggc | 840 |
| ggttccggtg | gcggctccgg | ttccggtgat | tttgattatg | aaaaaatggc aaacgctaat | 900 |
| aagggggcta | tgaccgaaaa | tgccgatgaa | aacgcgctac | agtctgacgc taaaggcaaa | 960 |
| cttgattctg | tcgctactga | ttacggtgct | gctatcgatg | gtttcattgg tgacgtttcc | 1020 |
| ggccttgcta | atggtaatgg | tgctactggt | gattttgctg | gctctaattc ccaaatggct | 1080 |
| caagtcggtg | acggtgataa | ttcaccttta | atgaataatt | tccgtcaata tttaccttct | 1140 |
| ttgcctcagt | cggttgaatg | tcgcccttat | gtctttggcg | ctggtaaacc atatgaattt | 1200 |
| tctattgatt | gtgacaaaat | aaacttattc | cgtggtgtct | ttgcgtttct tttatatgtt | 1260 |
| gccacctta | tgtatgtatt | ttcgacgttt | gctaacatac | tgcgtaataa ggagtcttaa | 1320 |

<210> SEQ ID NO 15
<211> LENGTH: 439
<212> TYPE: PRT
<213> ORGANISM: Artificial Sequence
<220> FEATURE:
<223> OTHER INFORMATION: synthetic

<400> SEQUENCE: 15

Val Lys Lys Leu Leu Phe Ala Ile Pro Leu Val Pro Phe Tyr Ser
1               5                   10                  15

His Ser Ser Glu Thr Val Thr Ser Gly Thr Ser Gly Tyr Pro Tyr Asp
            20                  25                  30

Val Pro Asp Tyr Ala Thr Ser Cys Leu Ala Lys Pro His Thr Glu Asn
        35                  40                  45

-continued

Ser Phe Thr Asn Val Trp Lys Asp Asp Lys Thr Leu Asp Arg Tyr Ala
    50                  55                  60

Asn Tyr Glu Gly Cys Leu Trp Asn Ala Thr Gly Val Val Cys Thr
65                  70                  75                  80

Gly Asp Glu Thr Gln Cys Tyr Gly Thr Trp Val Pro Ile Gly Leu Ala
                85                  90                  95

Ile Pro Glu Asn Glu Gly Gly Ser Glu Gly Gly Ser Glu Gly
            100                 105                 110

Gly Gly Ser Glu Gly Gly Thr Lys Pro Glu Tyr Gly Asp Thr
        115                 120                 125

Pro Ile Pro Gly Tyr Thr Tyr Ile Asn Pro Leu Asp Gly Thr Tyr Pro
    130                 135                 140

Pro Gly Thr Glu Gln Asn Pro Ala Asn Pro Asn Pro Ser Leu Glu Glu
145                 150                 155                 160

Ser Gln Pro Leu Asn Thr Phe Met Phe Gln Asn Asn Arg Phe Arg Asn
                165                 170                 175

Arg Gln Gly Ala Leu Thr Val Tyr Thr Gly Thr Val Thr Gln Gly Thr
                180                 185                 190

Asp Pro Val Lys Thr Tyr Gln Tyr Thr Pro Val Ser Ser Lys Ala
            195                 200                 205

Met Tyr Asp Ala Tyr Trp Asn Gly Lys Phe Arg Asp Cys Ala Phe His
    210                 215                 220

Ser Gly Phe Asn Glu Asp Pro Phe Val Cys Glu Tyr Gln Gly Gln Ser
225                 230                 235                 240

Ser Asp Leu Pro Gln Pro Val Asn Ala Gly Gly Ser Gly Gly
                245                 250                 255

Gly Ser Gly Gly Gly Ser Glu Gly Gly Gly Ser Glu Gly Gly Gly Ser
            260                 265                 270

Glu Gly Gly Gly Ser Glu Gly Gly Gly Ser Gly Gly Gly Ser Gly Ser
        275                 280                 285

Gly Asp Phe Asp Tyr Glu Lys Met Ala Asn Ala Asn Lys Gly Ala Met
    290                 295                 300

Thr Glu Asn Ala Asp Glu Asn Ala Leu Gln Ser Asp Ala Lys Gly Lys
305                 310                 315                 320

Leu Asp Ser Val Ala Thr Asp Tyr Gly Ala Ala Ile Asp Gly Phe Ile
                325                 330                 335

Gly Asp Val Ser Gly Leu Ala Asn Gly Asn Gly Ala Thr Gly Asp Phe
                340                 345                 350

Ala Gly Ser Asn Ser Gln Met Ala Gln Val Gly Asp Gly Asp Asn Ser
            355                 360                 365

Pro Leu Met Asn Asn Phe Arg Gln Tyr Leu Pro Ser Leu Pro Gln Ser
    370                 375                 380

Val Glu Cys Arg Pro Tyr Val Phe Gly Ala Gly Lys Pro Tyr Glu Phe
385                 390                 395                 400

Ser Ile Asp Cys Asp Lys Ile Asn Leu Phe Arg Gly Val Phe Ala Phe
                405                 410                 415

Leu Leu Tyr Val Ala Thr Phe Met Tyr Val Phe Ser Thr Phe Ala Asn
                420                 425                 430

Ile Leu Arg Asn Lys Glu Ser
            435

<210> SEQ ID NO 16
<211> LENGTH: 222

<212> TYPE: DNA
<213> ORGANISM: Artificial Sequence
<220> FEATURE:
<223> OTHER INFORMATION: synthetic

<400> SEQUENCE: 16

```
atgaaaaagt ctttagtcct caaagcctcc gtagccgttg ctaccctcgt tccgatgctg      60
tctttcgccg cggagggtga cgatcccgcc aaggcggcct ttgactccct gcaagcctca    120
gcgaccgaat atatcggtta tgcgtgggcg atggttgttg tcattgtcgg cgcaactatc    180
ggtatcaagc tgtttaagaa attcacctcg aaagcaagct ga                        222
```

<210> SEQ ID NO 17
<211> LENGTH: 73
<212> TYPE: PRT
<213> ORGANISM: Artificial Sequence
<220> FEATURE:
<223> OTHER INFORMATION: synthetic

<400> SEQUENCE: 17

Met Lys Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
            20                  25                  30

Ala Phe Asp Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70

<210> SEQ ID NO 18
<211> LENGTH: 276
<212> TYPE: DNA
<213> ORGANISM: Artificial Sequence
<220> FEATURE:
<223> OTHER INFORMATION: synthetic

<400> SEQUENCE: 18

```
gggtcagaag tgtccgacaa acgcacatgc gtgtctctga cgacccaacg cttaccggtt     60
tcgcgcatta agacgtatac cattaccgag ggtagtttgc gtgctgtcat ctttatcacc    120
aaacgtggcc tgaaagtgtg tgcagatccg caagcgacat gggttcgcga tgtagtccgt    180
agcatggatc gcaaaagcaa tacccggaac aacatgattc agacgaaacc aaccggtact    240
cagcagtcga cgaatactgc cgtaaccctg actggc                              276
```

<210> SEQ ID NO 19
<211> LENGTH: 92
<212> TYPE: PRT
<213> ORGANISM: Artificial Sequence
<220> FEATURE:
<223> OTHER INFORMATION: synthetic

<400> SEQUENCE: 19

Gly Ser Glu Val Ser Asp Lys Arg Thr Cys Val Ser Leu Thr Thr Gln
1               5                   10                  15

Arg Leu Pro Val Ser Arg Ile Lys Thr Tyr Thr Ile Thr Glu Gly Ser
            20                  25                  30

Leu Arg Ala Val Ile Phe Ile Thr Lys Arg Gly Leu Lys Val Cys Ala
        35                  40                  45

-continued

```
Asp Pro Gln Ala Thr Trp Val Arg Asp Val Val Arg Ser Met Asp Arg
    50                  55                  60

Lys Ser Asn Thr Arg Asn Asn Met Ile Gln Thr Lys Pro Thr Gly Thr
65                  70                  75                  80

Gln Gln Ser Thr Asn Thr Ala Val Thr Leu Thr Gly
                85                  90
```

PHAGE CONJUGATES AND USES THEREOF

CROSS-REFERENCE TO RELATED APPLICATIONS

This application is a 371 of PCT/IB2018/050525, filed Jan. 29, 2018, which claims the benefit of Italian Patent Application No. 102017000009270, filed Jan. 27, 2017.

FIELD OF THE INVENTION

The present invention relates to pharmaceutical compositions comprising lipid-bacteriophage conjugates, wherein the bacteriophage:lipid ratio is comprised between 3:1 to 100:1 and wherein the lipid is an immunologically active lipid and the bacteriophage is a filamentous bacteriophage, and uses thereof. Preferably, the bacteriophage is engineered to stimulate an immune response and/or bind to a target cell.

BACKGROUND OF THE INVENTION

The immune system is able to recognize lipids and the latter have multiple functions including immunoregulatory activities, surveillance against tumours and protection in case of infections (De Libero G and Mori L., 2012). In particular, lipid molecules are able to activate both the innate immune response and the adaptive response.

In this context, NKT invariant cells (iNKTs) represent a subpopulation of T cells with a function in the innate response, are present in the spleen, liver and bone marrow, express an NK-receptor and a semi-invariant T receptor characterized by a Valpha14-Jalpha18 gene rearrangement in mice and a Valpha24-Jalpha18 in humans, together with a limited number of Vbeta chains. iNKT cells recognize glycolipid antigens presented by CD1d molecules expressed by antigen-presenting cells such as dendritic cells. iNKT cells have potent immunomodulatory activity due to their ability to secrete Th1 and Th2 type cytokines and their activity is associated with resistance to tumours and protection against pathogens. The role of iNKT cells in cancer response was initially discovered through the identification of alpha-Galactosylceramide (aGalCer), a glycolipid derived from the marine sponge *Agelas mauritianus*, during a screening of natural products with anti-tumour activity. In response to aGalCer, iNKT cells rapidly synthesize a large amount of cytokines, which in turn activate a variety of cell populations including NK cells, dendritic cells (DCs), B and T lymphocytes. Through this activation cascade, aGalCer exercises a powerful anti-tumour action and has in vivo adjuvant activity, making it a promising candidate for an adjuvant therapy against cancer. The structure of the active ingredient has been identified and slightly modified for optimal efficiency in the production of the commercial compound referred to as KRN7000. KRN7000 is a synthetic analogue of alpha-Galactosylceramide. It is a specific ligand of human and murine iNKT cells and also a ligand of the CD1d protein. KRN7000 protects against shocks due to LPS and shows antitumour activity in various models. It has the following formula:

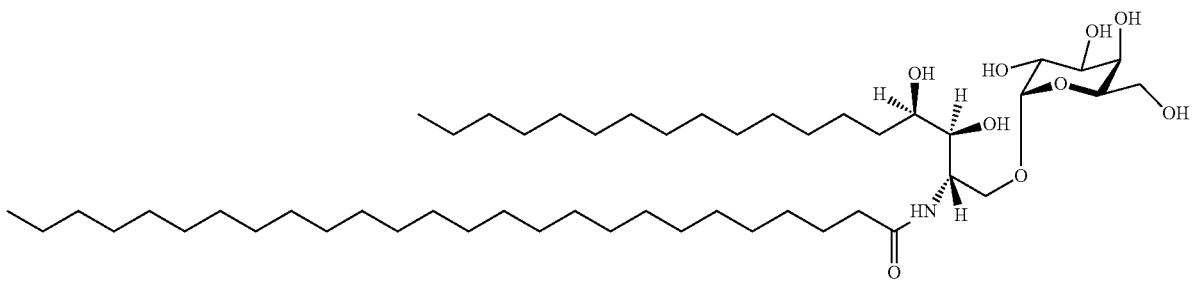

Following this discovery, various attempts were made to exploit these properties in human immunotherapy. However, although the drug was well tolerated, a weak clinical response was observed in patients receiving repeated KRN7000 administration. The studies carried out in the animal model have later shown that aGalCer induces long term cell anergy of iNKT cells, preventing the release of cytokines after recall stimulations (Sullivan B A and Kronenberg M, 2005). The mechanism of the anergy of iNKT cells induced by aGalCer has not yet been explained. One of the possible causes was assumed to be the lack of expression of costimulatory molecules by the antigen-presenting cells. It is in fact known that costimulation and cytokine signals produced by the professional-presenting cells such as the dendritic cells are necessary to avoid the anergy of NKTs, and therefore there is a need to preferably vehiculate the aGalCer to the so-called professional cells, as are also defined the dendritic cells (Thapa P et al., 2009). In this context, the inventors have recently described (Sartorius R et al., 2015) the construction and effectiveness of bacteriophage vectors specifically engineered to intercept murine dendritic cells by expressing in the pIII capsid protein the phage virions of the single chain fragment of the murine monoclonal anti-DEC-205 antibody, which recognizes a receptor specifically expressed by the mouse dendritic cells.

The design of dendritic cell-targeting strategies is a promising approach to improve the effectiveness of a vaccine. Recently, the CD141+ (XCR1+) dendritic cell subset has been described as the subpopulation of human dendritic cells specialized in the cross-presentation of exogenous antigens and in the induction of a strong cytotoxic T response, thus representing the ideal target for a DC-based vaccine. On the other hand, the simultaneous targeting of multiple DC subgroups such as CD303+, CD1c+ and CD14+ DCs seems to enhance the immune response, thanks to the crosstalk mediated by the cytokines released by these different subsets of human DCs (Sehgal K et al., 2014).

WO2006095345 describes the construction of phage conjugates through a linker to a variety of chemical compounds, essentially antibiotics and antifungals.

EP2910239 relates to bacteriophages encapsulated in a lipid or mixture of lipids which form vesicles or liposome-like particles in order to increase the stability and the half-life of bacteriophages, e.g. in the animal digestive tract.

WO2001005950 relates to a method for exposing peptides/proteins on the surface of the phage by forming a disulfide bridge between the phage coat protein and the protein/peptide to be exposed. The document does not relate to the lipids vehiculation.

WO20130138716 refers to a bacteriophage with LPS on the surface used as angiogenesis modulator. Since phages are produced in bacteria, they naturally express lipopolysaccharides on their surface, therefore they are not suitable for human administration.

EP1088889 relates to the engineering of the bacteriophage for the expression of a cytotoxic epitope, therefore it relates to the peptide vehiculation, not to the lipid one.

Therefore, there is still the need to develop a system to vehiculate immunologically active lipids which enhances its activity or directs it to specific cell subpopulations.

SUMMARY OF THE INVENTION

The present invention consists in the construction of filamentous bacteriophages fd conjugated with immunologically active lipids such as (but not exclusively) the alpha-Galactosylceramide (aGalCer) glycolipid. Thanks to the high content of hydrophobic residues, the major protein (pVIII) of the bacteriophage capsid has high binding affinity with lipid molecules.

The present invention allows to vehiculate immunologically active lipids, i.e. capable of activating the cells of the immune system, and therefore of enhancing the innate and adaptive immune response of the organism itself, even if it does not act directly on the cell that is the object or cause of the disease. The effect of the lipid is increased by the delivery system itself, which also allows to overcome the limits of the lipid itself, such as the ability to induce tolerance after numerous administrations.

As an example of the functional activity of lipid conjugates with phage particles, the inventors provide experimental evidence that the filamentous bacteriophages conjugated with aGalCer, as opposed to soluble aGalCer, are able to induce repeated stimulation of iNKT cells in vitro and in vivo without inducing anergy. Furthermore, the inventors have observed that the simultaneous vehiculation in the same phage particle of aGalCer and an antigenic peptide induces an optimal adaptive response by antigen-specific CD8+ T cells. Finally, it is shown that a therapeutic vaccination with the aforementioned phage particles is able to inhibit the growth of tumours administered to the experimental animal. The present results indicate that the filamentous bacteriophage represents an optimal system for lipid vehiculation and, as in the case of fdWT/aGalCer particles, it has applications in the immunotherapy of tumours.

Furthermore, in order to make this vehiculation system translational for possible immunotherapy applications in humans, bacteriophages have been constructed to recognize specific receptors expressed on one or more subpopulations of human dendritic cells, and therefore able of being specifically vehiculated to human dendritic cells.

The filamentous bacteriophage fd, a non-lytic and non-pathogenic virus for humans, capable of infecting and replicating only in *Escherichia coli* bacterial cells which carry an F' episome, was used to generate the bacteriophage/aGalCer conjugate. The bacteriophage fd (~7 nm×800 nm) consists of a single-stranded circular DNA genome of approximately 6400 nucleotides, surrounded by 2750 copies of an α-helix protein of about 50 amino acids (pVIII) and some copies of minor proteins that make up its ends.

The pVIII is arranged to form a tubular coating protecting the phage genome, and its high content of hydrophobic residues gives it high binding affinity to lipids such as bacterial LPS, and therefore to glycolipids such as aGalCer. Furthermore, the gpVIII sequence in the phage genome was engineered for the expression of short exogenous sequences at the N terminal of the pVIII protein, which can be exposed on the phage surface in high number of copies (Malik, P. & Perham, 1996).

Bacteriophage particles purified from bacterial lipopolysaccharides (LPS) were conjugated with KRN7000 synthetic aGalCer in a ratio of 10:1, and the present invention was used to trigger the iNKT response in vivo and in vitro. The aGalCer vehiculated by phage particles proved to be presented by mouse bone marrow-derived dendritic cells (BMDC) and to activate an iNKT hybridoma cell line.

In addition, spleen cells of mice injected with bacteriophages loaded with aGalCer and restimulated in vitro with free aGalCer are still able to proliferate and produce cytokines such as interleukin 2 (IL-2), in contrast to what happens when unconjugated aGalCer is injected.

The co-vehiculation of aGalCer and of a model antigen, represented by the OVA CD8a+ peptide (SIINKFEKL, SEQ ID No. 1) derived from chicken ovalbumin, on the bacteriophage scaffold, is able to optimize the adaptive response of CD8+ T cells. In fact, the frequency of SIINFEKL OVA CD8+ T cells (SEQ ID No. 1) which produce IFN-gamma is higher in those mice that have been injected once or twice with fdOVA/aGalCer, compared to mice injected twice with the bacteriophage only vehiculating the OVA peptide. Finally, in therapeutic vaccination experiments, the administration of fdWT/aGalCer conjugate proved to be able to induce tumour regression in laboratory mice implanted with the B16 melanoma cell line.

The filamentous phages have also been further engineered for the specific vehiculation to the subpopulations of human dendritic cells. More specifically, the inventors created phage particles expressing the single chain antibody fragment (scFv) directed against the DEC 205 receptor. This receptor is expressed on type I and type II myeloid dendritic cells (DCs) and on plasmacytoid DCs. The inventors also created phage particles expressing the XCL1 chemokine, for exclusive targeting to XCR1+ dendritic cells with a cross-presentation function. These bacteriophages are able to be internalized by subpopulations of human dendritic cells isolated from venous blood (FIG. 5).

The systems of the invention may be exploited for the specific targeting of phage formulations, whether based on the aGalCer vehiculation or not, to different subpopulations of human dendritic cells.

Bacteriophages infect and proliferate only in their hosts (bacteria). For this reason their administration to humans can be considered safe. Furthermore, their production is relatively simple and economically advantageous.

Phages are of considerable industrial interest and their use as antibacterials is currently subject to several clinical trials. Thanks to their anti-bacterial action they are also used in the food industry.

Therefore, the present invention provides a pharmaceutical composition comprising lipid-bacteriophage conjugates, wherein the bacteriophage:lipid ratio is comprised between 3:1 and 100:1 and wherein the lipid is an immunologically active lipid and the bacteriophage is a filamentous bacteriophage.

Preferably, the ratio bacteriophage:lipid is in a range of 5:1 to 80:1, preferably the ratio bacteriophage:lipid is in a range of 10:1 to 50:1. Preferably, the ratio bacteriophage:lipid is 3:1, 5:1 or 10:1. Preferably, the bacteriophage is linked to at least one lipid via a non-covalent interaction.

Preferably, the immunologically active lipid is selected from the group consisting of: aGalCer, glycosphingolipids, palmitoyl-2-arachidonoyl-sn-glycero-3-phosphocholine (PAPC), monophosphoryl lipid A and their natural or synthetic analogues. Preferably, the immunologically active lipid is selected from the group consisting of: aGalCer, and other natural Agelasfines, the synthetic form of the KRN7000 alpha-Galactosylceramide; other synthetic analogues of alpha-Galactosylceramide such as 7DW8-5; other bacterial or microbic α-linked glycosphingolipids; palmitoyl-2-arachidonoyl-sn-glycero-3-phosphocholine (PAPC) and its oxidized form (OXPAPC), and other mixtures of oxidized phospholipid; monophosphoryl lipid A (MPL-A) and its synthetic analogues.

In a preferred embodiment, the bacteriophage is a filamentous bacteriophage engineered or genetically modified to express an exogenous sequence, wherein said exogenous sequence stimulates an immune response and/or selectively binds to a cell surface molecule on a target cell.

Preferably, the bacteriophage is a filamentous bacteriophage whose genome has been engineered to clone an exogenous sequence or fragment thereof in the 5' region of a gene encoding a phage coat protein, and wherein said exogenous sequence stimulates an immune response and/or selectively binds to a cell surface molecule on a target cell. Still preferably, the exogenous sequence or fragment thereof is encoded by a nucleic acid fused to the gene(s) encoding the pVIII and/or pIII proteins of the coating of the bacteriophage.

In the present invention the immune response can be assessed based on the proliferative ability of T or iNKT cells; the production of cytokines such as IL2 or Interferon gamma by T or iNKT cells; ex vivo analysis of antigen-specific T-cell induction by staining with MHC-peptide dextramers and cytofluorimetric analysis; the activation analysis of dendritic cells, in vivo experiments on animal models.

In a preferred embodiment, the exogenous sequence or a fragment thereof is encoded by a nucleic acid fused to a nucleotide sequence encoding a bacteriophage coat protein.

Preferably, the exogenous sequence encodes a protein or a fragment thereof, an antibody or a fragment thereof, or a chemokine.

Still preferably, the protein is ovalbumin, the antibody is directed against the DEC205 receptor and the chemokine is XCL1. Preferably, the antibody against the DEC205 receptor and the chemokine XCL1 comprise the sequences as disclosed below. In a preferred embodiment, the coat protein is the pIII protein (wild type amino acid sequence according to the Accession number P03661 GeneID: 22475004) or the pVIII protein (wild type amino acid sequence according to the Accession number P69539.1 GeneID:22475003).

The "accession numbers" correspond respectively to the wild type sequences of the pIII and pVIII proteins of the filamentous bacteriophage fd. In the present invention these sequences have been modified through the site-directed mutagenesis for the insertion of restriction enzyme sites useful for the directional cloning of exogenous sequences.

In a preferred embodiment, the coat protein comprises SEQ ID NO: 13 or SEQ ID NO: 15 or SEQ ID NO: 17.

In a preferred embodiment, the target cell is a dendritic cell, preferably a type I or type II myeloid dendritric cell, or a plasmacytoid dendritic cell.

In a preferred embodiment, the bacteriophage is bound to a combination of lipids. For example, the combination comprises at least two, three, four lipids as specified above.

In a preferred embodiment, the filamentous bacteriophage is selected from the group consisting of: M13, fd and f1.

In a preferred embodiment, the composition further comprises pharmaceutically acceptable excipients, vehicles or diluents.

Preferably, the composition is intended for use in the treatment of a hyperproliferative infection or disease.

Preferably, the hyperproliferative disease is a tumour, preferably, but not exclusively, a melanoma.

Preferably, the infection is a bacterial, viral, parasitic, yeast, fungal infection which is still not effectively protected by prophylactic or therapeutic vaccines such as: Chagas disease, Zika virus, Dengue virus.

In the present invention, an exogenous sequence is a nucleotide or amino acid sequence not belonging to the wild type protein or gene. It is usually added by recombinant DNA technology.

In the present invention, a target cell is a cell to which a molecule or the cytotoxic cell activity is directed.

Dendritic cells refer to cells of the immune system apt to present the antigen, discovered by R. Steinmann.

The present invention relates to the field of drug delivery. More specifically, the invention relates to the preparation and use of bacteriophages, preferably genetically modified to obtain a specificity towards the target cells.

Bacteriophages

In the present invention a bacteriophage is a virus infecting and replicating in bacteria.

The terms "bacteriophage" and "phage" are used interchangeably in the present document to refer to a bacterial virus forming a package consisting of a protein coat which contains nucleic acid needed for replication. The nucleic acid can be DNA or RNA, be double- or single-stranded, linear or circular. Unless otherwise specified, the terms "bacteriophage" and "phage" also include "phagemid", i.e. a bacteriophage whose genome comprises a plasmid which can be removed and packed by co-infection of a host with a phage helper.

According to a first aspect, the invention provides a lipid-conjugated bacteriophage. The bacteriophage is non-covalently bound to the lipid. The bacteriophage is a filamentous phage. The filamentous phage may be a filamentous phage specific for *E. coli* including, but not limited to: M13, fd and f1. The phage particle may include a genetically modified phage vector or a genetically modified hybrid vector (phagemid).

A wide range of phage, phagemids and helper vectors are known to those skilled in the art (e.g. see Kay et al, 1996; Berdichevsky et al, 1999; Benhar, 2001).

According to the present invention, the phage genome can be genetically modified to express a target ligand (targeting), as described below. Genetic modification can also be used to create properties that are not related to targeting. For example, the modification can help allowing the phage to delay inactivation from any host defence system (e.g. see U.S. Pat. No. 5,766,892). Genetic modification may allow the delivery and expression of genes in the target cell, as described below. Methods for creating genetically modified phages are well known in the art (e.g. see Sambrook et al., 1989). For the construction of lipid-bacteriophage conjugates, phages may be propagated and maintained using methods well known in the art (Sambrook et al., 1989, Kay et al., 1996 and the examples therein). For the commercial-scale production of these conjugates, large scale methods for producing bacteriophages can be used (e.g. see WO 2004/052274).

Lipids

The term immunologically active lipid refers to a lipid able to activate the immune system. It is in fact known that lipid molecules can be recognized by both innate and adaptive immune systems. More specifically, oxidized phospholipids derived from 1-palmitoyl-2arachidonoyl-sn-glycero-3-phosphorylcholine (PAPC) are able to promote the immune response as representatives of molecules defined as "damage associated molecular patterns (DAMS)" (Zanoni I et al 2016). In addition, glycolipids such as alpha galactosylceramide or microbial glycolipids stimulate the response of NKT cells (Zajonc and Girardi 2015). Finally, as regards the adaptive immunity, there is also a fraction of T lymphocytes able to recognize lipid molecules presented to them by "non-classical MHC molecules" (De Libero G and Mori L 2005).

The lipids of the invention have a therapeutic effect on a target disorder or condition. The term "therapeutic effect" refers to an effect that reverses, stops, slows progression, improves or alleviates the symptoms of a disorder or condition.

The lipids forming the conjugates of the invention are bound to the outer surface of the bacteriophage. In other words, the lipid is exposed to the external environment and not enclosed within a viral capsid or a viral particle. The lipid is not bound covalently to the outer surface of a bacteriophage coat protein (see materials and methods).

The bacteriophage can be linked to a combination of multiple lipids.

The term "conjugate" comprises non-covalent bonds between the phage and the lipid. The bacteriophage may be conjugated with other functional groups modulating the immunogenicity, the pharmacokinetics and/or the pharmacodynamics of the lipid-bacteriophage conjugate. As a non-limiting example, the lipid-bacteriophage conjugate can be pegylated (i.e. conjugated with polyethylene glycol), thus resulting in decreased immunogenicity (e.g. see US 2004/0161431). Such conjugations can be performed before or after the conjugation to the lipid, and typically involve a conjugation method other than that used to combine the lipid with the bacteriophage. For example, surface modifiers can be conjugated with a thiol group engineered in the coat protein, using methods well known in the art.

Binders and Target Cells

In another aspect, the invention provides a lipid-bacteriophage conjugate expressing an exogenous targeting sequence (binder) which stimulates an immune response and/or binds selectively to a surface molecule on a target cell. The term "exogenous targeting sequence", as used herein, comprises sequences that are not naturally expressed on a bacteriophage coat, either expressed by a genetically modified bacteriophage or related to the bacteriophage by means of genetic modification, chemical conjugation, or both. The targeting sequence and its mode of expression or linkage was designed to facilitate the lipid-bacteriophage conjugate to selectively bind to a target cell. This term further comprises a targeting sequence comprising a phage-conjugated ligand which binds non-covalently to a second target molecule able to bind to the target cell.

The bacteriophage can be genetically modified to selectively bind to a target cell. Genetic modification can cause the expression of a ligand on the phage coat. Genetic modification may be in the form of a DNA sequence encoding target fused to a gene encoding a phage coat protein. Phages exposing foreign proteins or peptides as a fusion with a phage-coat protein are well known to those skilled in the art. A variety of phages and coat proteins may be used, including, but not limited to: M13 proteins III, M13 protein VIII, M13 proteins VI, M13 proteins VI, M13 protein IX, fd minor coat protein pIII (Saggio et al., 1995; Uppala and Koivunen, 2000), fd coat protein pVIII (Sternberg and Hoess, 1995; Mikawa et al, 1996), fr coat protein (WO 96/11947), F29 tail proteins GP9 (Lee and Guo, 1995), MS2 coat protein, T4 SOC, HOC, IPIII and fibritin proteins (Hong and Black, 1993; Heal et al., 1999; Efimov et al., 1995; Ren and Black, 1998), PRD-1 gene III, QB3 capsid protein and P22 tailspike protein (Carbonell and Villaverde, 1996). In the preferred filamentous phage system, a wide range of vectors is available (see Kay et al, 1996; Berdichevsky et al, 1999; Benhar, 2001). In a preferred embodiment, the binder is expressed in fusion with the capsid protein (protein VIII) of a filamentous phage or with the minor capsid protein (protein III) of a filamentous phage.

A nucleic acid sequence encoding the targeting sequence can be obtained from its natural source, either as a whole (i.e. complete) gene or a portion thereof. A nucleic acid molecule can be produced using recombinant DNA technology (for example, polymerase chain reaction (PCR), cloning) or chemical synthesis. Nucleic acid sequences include sequences of natural nucleic acids and their homologues, including, but not limited to, natural allelic variants and modified nucleic acid sequences in which nucleotides have been inserted, deleted, substituted, and/or inverted so that such modifications substantially do not interfere with the ability of the nucleic acid molecule to encode a functional targeting residue of the present invention. A homologue of a nucleic acid molecule can be produced using a plurality of methods known to those skilled in the art (e.g. see Sambrook et al., 1989). The methods for the insertion of exogenous coding sequences in a phage gene are well known (e.g. see Sambrook et al, 1989; Brent et al, 2003). Some non-limiting examples of the genetic modification of a bacteriophage in order to make it express exogenous sequences are disclosed in the examples below.

Alternatively, a target sequence of the invention can be synthesized using any recombinant or synthetic method known in the art. The term "analogues" refers to peptides or polypeptides obtained by substitution, deletion or addition of amino acid residues in the sequence, optionally also the use of a chemically derivatised residue instead of a non-derivatised residue, as long as they maintain their capacity to bind the desired target molecule.

The target sequence is any sequence with specific binding properties with respect to a selected target cell. The sequence may be a sequence encoding an antibody, including, but not limited to: monoclonal antibodies, polyclonal antibodies and antibody fragments, such as recombinant antibody fragments, single chain antibodies (scFv), single variable domains of antibodies and the like (Borrebaeck, 1995; Lo, 2003). The methods of generating monoclonal and polyclonal antibodies are well known in the art. Antibodies can be generated using any of the several known methods. Furthermore, the techniques can be used to modify a "murine" antibody into a "human" antibody, without altering the binding specificity of the antibody.

The target sequence can also encode a protein or a peptide having binding specificity with respect to the target cell or it can also encode a peptide selected from a library of peptide sequences having binding specificity with respect to the target cell (Kay et al., 1996). Methods for building libraries and their use for screening ligands having affinity for a target molecule or cells are known in the art (see, e.g. Kay et al., 1996).

The ligand is chosen depending on the specific conjugate, the target cell and the disorder to be treated. For some applications, the ligands are chosen in such a way that they are internalized by the target cell from the binding of the target molecule, thus allowing the internalization of the lipid-carrying bacteriophage. Methods of construction and selection for the internalization of phages are known in the art (e.g. see Becerril et al., 1999, Kassner et al., 1999, Poul and Marks, 1999, Larocca and Baird, 2001, Larocca et al., 2001, Urbanelli et al., 2001, U.S. Pat. Nos. 6,451,527, 6,448,083, and International Application WO 98/05344). For other applications, the lipid-bacteriophage conjugate is not internalized and the lipid penetrates into the cell, or acts in the extracellular compartment.

The exogenous sequence expressing the lipid-bacteriophage of the invention is selected so as to facilitate the selective binding of the conjugate to a target cell involved in a disease or disorder in a subject who needs it. The target cell can be a bacterial cell, a fungal cell, a yeast cell, a unicellular parasitic cell, multicellular parasitic cells, a virus-infected mammal cell, a microorganism-infected mammal cell, a parasite-infected mammal cell, a tumour cell, a cell supporting tumour growth such as tumour vessels, an immune cell involved in the development of an autoimmune disease, and any sick or malfunctioning cell which can be targeted through a distinct surface molecule.

The subject who needs it is a human subject, a mammal or a non-mammalian animal. The target cell may also be a cell of the immune system with the function of antigen presenting cell. The target cell may also belong to a healthy subject and, in this case, the conjugate acts as a vaccine.

Pharmaceutical Compositions

The invention provides pharmaceutical compositions comprising the lipid-bacteriophage conjugates of the invention. The term pharmaceutical composition, as used herein, also includes compositions suitable for veterinary use.

Pharmaceutical compositions can be prepared by mixing an amount of a purified lipid-bacteriophage with a pharmaceutically acceptable vehicle. For example, the compositions of the present invention may be administered in the form of injectable compositions. A typical composition for this purpose includes a pharmaceutically acceptable vehicle. For example, the composition may contain human serum albumin and NaCl-containing phosphate buffer. Other pharmaceutically acceptable vehicles comprise aqueous solutions, non-toxic excipients, including salts, preservatives, buffers and the like, as described in Pharmaceutical Sciences of Remington, 1975. Examples of non-aqueous solvents include propylene glycol, polyethylene glycol, vegetable oils and injectable organic esters, such as ethyl oleate. Aqueous vehicles may include water, alcoholic/aqueous solutions, saline solutions, parenteral vehicles such as sodium chloride, dextrose, Ringer's ones and the like. Intravenous vehicles are fluid and nutrients. Preservatives are antimicrobials, antioxidants, chelating agents and inert gases. The pH and the exact concentration of the various components of the bacteriophage pharmaceutical compositions of the invention may be adjusted according to the routine of the art (Goodman and Gilman, 1990).

Thanks to the stability of phages in the gastrointestinal tract, they are also suitable as oral formulations, e.g. for the treatment of systemic infections. Oral compositions generally comprise an inert diluent or an edible support and can be compressed into tablets or enclosed in gelatin capsules. Tablets, pIIIs, capsules and the like can contain any of the following ingredients, or compounds of a similar nature: a binder such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a colloidal silicon dioxide; a sweetening agent such as sucrose or saccharin; and a flavoring agent such as peppermint, methyl salicylate and fruit flavors. When the dosage unit form is a capsule, it may contain, in addition to materials of the above-mentioned type, a liquid vehicle such as a fatty oil. Alternatively, the pharmaceutical compositions of the present invention may be in the form of liposomes, lipophilic microcapsules, dendrimers or the like for oral administration. Those skilled in the art are able to prepare the bacteriophage compositions of the present invention in the form of lipophilic microcapsules, a dendrimer or a liposome using conventional techniques known in the art. Lipid-bacteriophage preparations of the invention can also be administered with food.

The person skilled in the art is able to provide a bacteriophage composition which can be administered intratumourally, subcutaneously, intranasally, rectally, transdermally, topically, or through other known routes of drug administration. Solutions or suspensions used for parenteral, intradermal, subcutaneous or topical application may include any of the following components: a sterile diluent such as water for injection, saline solution, fixed oil, polyethylene glycol, glycerine, propylene glycol or other synthetic solvents; antimicrobic agents such as benzyl alcohol and methyl parabens; antioxidants such as ascorbic acid or sodium bisulfite; chelating agents such as ethylenediaminetetraacetic acid (EDTA); buffers such as acetates, citrates and phosphates, and agents for adjusting toxicity such as sodium chloride or dextrose. Parenteral preparations may be enclosed in ampoules, disposable syringes or multiple single-dose vials made of glass, plastic or other suitable material.

The phage can also be mixed with other active materials which do not compromise the desired action or with materials which complete the desired action.

Therapeutic Use

The conjugates provided herein are useful in the treatment and prevention of various diseases, syndromes and disorders, including, but not limited to: hyperproliferative disorders, tumours, such as melanomas.

In the present invention, the term "treatment" refers to any manner in which the symptoms of a condition, disorder or disease are ameliorated.

In an embodiment, the lipid-bacteriophage conjugates of the present invention may be used for the treatment of tumours. In these diseases, cell growth is excessive or uncontrolled. Tumours suitable for treatment in the context of this invention include, but are not limited to, breast tumours, gliomas, melanomas, prostate cancer, hepatomas, sarcomas, lymphomas, leukemias, ovarian tumours, thymomas, nephroma, pancreatic cancer, colon cancer, head and neck cancer, stomach cancer, lung cancer, mesothelioma, myeloma, neuroblastoma, retinoblastoma, cervical cancer, endometrial cancer and cutaneous squamous cell carcinoma. For such treatments, binders may be selected to bind to cell surface receptors that are generally preferentially expressed in tumours (e.g. MUC-1 and Tac). By administrating the compositions of the present invention, the undesired growth of cells can be slowed or stopped, thereby ameliorating the disease. More specifically, the methods used in the present invention are expressly aimed at killing or stopping the proliferation of tumour cells.

The compositions of the present invention may also be used to treat a subject having an infection, including, but not limited to: a bacterial infection, a viral infection, a yeast infection, a fungal infection and a parasitic infection.

The compositions of the present invention are preferably administered subcutaneously, intratumourally, intravenously, intranasally, orally, topically, etc., in an amount and for a period of time effective to treat the infection or the disease.

Determining the effective amount of the non-toxic lipid-bacteriophage conjugate composition for the host administered in accordance with the present invention involves standard assessments. The dosage and duration of the suitable treatment can be verified by those skilled in the art using known techniques. Compositions of lipid-bacteriophage conjugate for use in the treatment of diseases, conditions or infections as indicated above, may be used alone or in combination with multiple therapeutic agents, administered together or separately, e.g. before, simultaneously or after the administration of the pharmaceutical compositions of the invention.

In particular, lipid-bacteriophage conjugate compositions for the treatment of neoplasms can be used in combination with additional chemotherapeutic drugs or other anti-cancer agents well known in the art.

As used herein, "exogenous sequence" or "exogenous genetic material" refers to a polynucleotide (e.g. nucleic acid or oligonucleotide), natural or synthetic, which is not naturally found in a bacteriophage or in the event it is naturally found in the bacteriophage, is not transcribed or expressed at biologically significant levels by the bacteriophage. "Exogenous sequence" or "exogenous genetic material" includes a non-natural polynucleotide that can be transcribed into an antisense RNA, as well as all or part of a "heterologous gene" (i.e. a gene encoding a protein which is not expressed or is expressed at biologically insignificant levels in a "natural" bacteriophage). Thus, for example, the present invention includes the introduction into a target cell of an expression cassette comprising a recombinant gene containing an inducible promoter operably linked to a coding sequence of a therapeutic polynucleotide or oligonucleotide. In preferred embodiments, the exogenous genetic material of the bacteriophage can be both transcribed and translated into the target cell. Effective methods of generating such vectors and expression cassettes are known in the art (e.g. see Sambrook et al., 1989; Ausubel et al., 1994).

Methods for constructing and using phage vectors for gene expression for prokaryotic and eukaryotic cells are known in the art (WO 2004/062677, WO 98/05344 and U.S. Pat. No. 6,448,083, among many others).

BRIEF DESCRIPTION OF THE DRAWINGS

The present invention will be described by means of non-limiting examples, with reference to the following figures.

DETAILED DESCRIPTION OF THE INVENTION

Materials and Methods

Purification of Phage Particles

Figure 1:
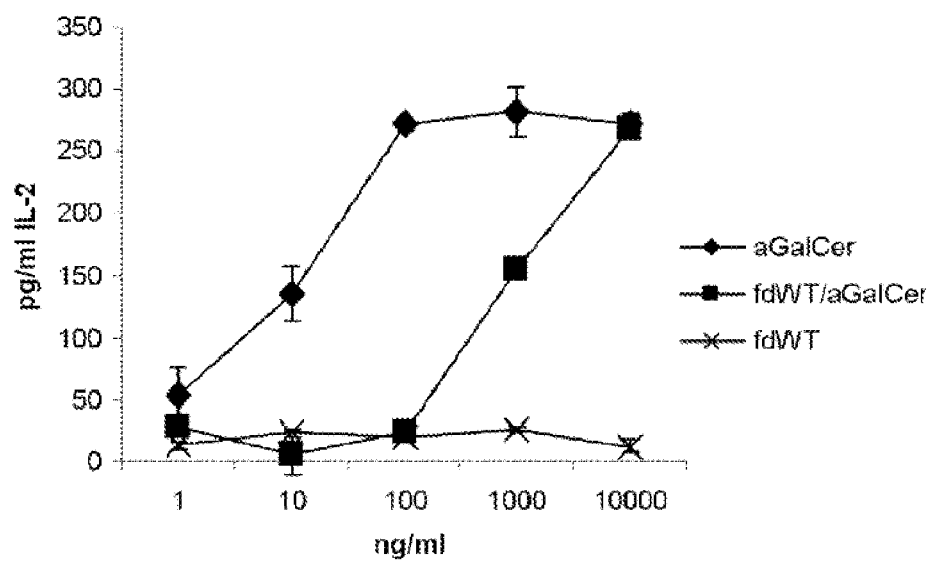
FIG. 1: The graph represents the response of the Va14i murine hybridoma to aGalCer vehiculated by phage particles. LPS-free Filamentous phages fd (fdAMPLAY388-HA (Sartorius R et al., 2011), hereinafter fdWT) were conjugated with aGalCer and internalized by dendritic cells for the presentation of aGalCer to the Va14 iNKT hybridoma cells. Soluble aGalCer was used as a control. The activation of iNKT hybridoma cells was assessed by ELISA assay of the IL-2 released in the culture medium and plotted in graph as pg/ml. (rhombs) soluble aGalCer; (crosses) bacteriophages fdAMPLAY388-HA (fdWT); (squares) aGalCer-conjugated bacteriophages (fdWT/aGalCer).

Filamentous bacteriophages fdAMPLAY388-HA (Sartorius R et al., 2011) were purified from supernatants of TG1rec0 *Escherichia coli* cells transformed with fdAMPLAY388-HA phage DNA (Sartorius R et al., 2011). The bacteria were grown in TY2X culture medium for 16 hours and the virions were precipitated from the *E. coli* culture supernatant by precipitation with PEG 6000 and sodium chloride. Phages were then purified on cesium chloride gradient and dialysed against PBS1X. The elimination of LPS from the phage particles was performed using Triton X-114 (Sigma-Aldrich). Briefly, the Triton X-114 was mixed to the phage preparations to a final concentration of 1% by vigorous vortex shaking. The mixture was incubated at 4° C. for 5 minutes, then incubated for 5 minutes at 50° C. and centrifuged (20.000 g, 10 minutes) at 2° C. The upper aqueous phase containing the virions was carefully removed and subjected to new separation with Triton X-114 for multiple cycles (7-10 cycles). The resulting aqueous phase containing the virions was subjected to cesium chloride gradient centrifugation, dialysed against PBS 1× and analysed for residual LPS contamination using a chromogenic assay (Limulus Amebocyte Lysate (LAL) QCL-1000™, Lonza), according to the manufacturer's instructions.

The fdOVA particles were generated using the genome of the fdOVA bacteriophage described above (Sartorius R et al., 2011), containing two copies of the pVIII protein, a wild type one and a modified one containing the DNA sequence encoding the OVA SIINFEKL peptide (SEQ ID No. 1) at 5' so that the SIINFEKL sequence (SEQ ID No. 1) is expressed between the amino acid 3 and 4 of pVIII.

To produce the fdOVA phage particles, the TG1rec0 bacteria transformed with the fdOVA phage genome were grown in the TY2X culture medium until reaching 0.24 OD At this time the expression of the recombinant OVA-pVIII proteins was induced by adding 0.1 mM isopropyl-beta-D-thiogalactopyranoside (Sigma-Aldrich) to bacterial cultures in TY2X medium. The growth continued for 16 h, at the end of which the virions were purified as described above.

Generation of Bacteriophages fdWT/aGalCer and fdOVA/aGalCer

The aGalCer-conjugated bacteriophages were produced by conjugating the synthetic analogue of aGalCer, KRN7000 (BML-SL232-1000, Vinci Biochem) to fdAMPLAY388-HA bacteriophages (Sartorius R et al., 2011) (hereinafter referred to as fdWT) and fdOVA bacteriophages (Sartorius R et al., 2011).

To generate fdWT/aGalCer and fdOVA/aGalCer bacteriophages, the phages in PBS pH 8 and the synthetic analogue of aGalCer, KRN7000 (BML-SL232-1000, Vinci Biochem) dissolved in DMSO were combined in a 10:1 molar ratio (phages:aGalCer) and incubated at 4° C. overnight on a rotating wheel. The virions were then subjected to cesium chloride gradient centrifugation, dialysed against PBS 1× and the concentration of bacteriophages was determined by spectrophotometer. The presence of aGalCer in phage preparations was determined by the in vitro biological assay described below.

Mice 6-8-week-old C57BL/6 mice were purchased at the Charles River and housed in the IGB-CNR animal house under standard conditions, in the absence of pathogens according to institutional guidelines.

In Vitro Stimulation of iNKT Cells

The dendritic cells (DCs) were derived from the bone marrow of C57BL/6 mice according to published methods (7). After seven days of culture, the DCs (50000 cells/well) were incubated for 2 hours with different concentrations of aGalCer (1, 10, 100, 1000, 10000 ng/ml) (KRN7000 BML-SL232-1000, Vinci Biochem) fdWT bacteriophages or fdWT/aGalCer bacteriophages (1, 10, 100, 1000, 10000 ng/ml), washed and incubated with the Va14 iNKT FF13 mouse hybridoma (Schumann J et al., 2007), kindly donated by Prof. Gennaro de Libero, Department of Biomedicine, University of Basel, (50000 cells/well) for 40 hours.

The interleukin 2 (IL-2) released from the cells in the culture supernatant was measured by ELISA using the IL-2 ELISA MAX™ standard mouse kit (Biolegend).

Measurement of the In Vivo Response to aGalCer After In Vitro Restimulation

The mice were injected intravenously with 100 micrograms of PBS containing 5 micrograms of KRN7000 aGalCer (BML-SL232-1000, Vinci Biochem), 50 ug of fdWT/aGalCer bacteriophages or only with the vehicle. After 24 h the mice were sacrificed, the spleens were harvested, and the cells were isolated. The splenocytes were plated in U-bottom 96-well plates at 2×10$^5$ cells per well in RPMI medium containing 10% FCS in the presence of increasing doses (0, 1, 10 or 100 ng/ml) of aGalCer or vehicle. For proliferation assays, 1 pCi of [3H] thymidine (PerkinElmer Life Sciences) was added to the wells after 60 hours of culture, and the cells were then cultured for another 12 hours. The cells were then collected using the automated FilterMate collector (PerkinElmer, CA, USA), and the amount of incorporated [3H] thymidine was assessed using a Top count NTX microplate scintillation counter (PerkinElmer). To measure the IL-2, cell culture supernatants were collected after 60 hours, and IL-2 cytokine levels were assessed by ELISA using the IL-2 standard ELISA MAX™ mouse kit (Biolegend).

Evaluation of the Specific In Vivo OVA CD8 T Response

Groups of mice (n=5) were inoculated by subcutaneous injection (day 0) with 50 micrograms of fdOVA bacteriophages (expressing the SIINFEKL peptide (SEQ ID No. 1)) or 50 micrograms of fdOVA/aGalCer bacteriophages and restimulated (day 14), with the same amount of fdOVA bacteriophages, whether they vehiculate the aGalCer or not. As a control, the mice were inoculated twice only with the vehicle (PBS).

At day 21, the splenocytes were isolated and the frequency of OVA-specific CD8+ T cells was assessed by staining and cytofluorimeter analysis using the anti-CD8a-PE/Cy7 antibody (cod. 100722 Biolegend) and KB-SIINFEKL dextramers (SEQ ID No. 1) PE conjugates (cod. Jd2163-PE, Immudex).

The effector cells producing IFN-g were assessed by culturing spleen cells in the presence of the SIINFEKL synthetic peptide (10 micrograms/ml, synthesized by Primm srl, Milan) and of brefeldin A (B7651-5MG cod, SIGMA) for 5 hours. The cells were then collected and the IFN-g production was assessed by intracellular staining on CD8+ T cells using the anti-IFN-g-PE mAb antibody (cod. 505808 Biolegend).

Therapeutic Vaccination Against B16 Tumour Cells

C57BL/6 mice (n=5/group) were inoculated with $2.5 \times 10^5$ B16 melanoma cells kindly provided by Dr. Dellabona (Istituto scientifico San Raffaele, Milan, Sartorius R et al., 2011) subcutaneously in the left side. When the tumours became palpable, the mice were vaccinated with PBS, 2.5 micrograms aGalCer, 50 micrograms of fdWT bacteriophages or 50 micrograms of fdWT/aGalCer in a total volume of 80 microliters. Tumour growth was assessed three times a week using a caliber and reported as tumour volume (in $mm^3$) according to the formula $(d^2 \times D)/2$, where d and D are the minor diameter and the major one, respectively. The mice were sacrificed when the size of the tumour had exceeded 1,500 $mm^3$, in compliance with the established guidelines. Survival was recorded as the percentage of surviving animals.

Construction of the fda-hDEC and fdXCL1 Bacteriophage Vectors fda-hDEC

The scFv against the DEC205 human receptor consists of the variable region of the light chain and the variable region of the heavy chain of the anti-DEC205 monoclonal antibody, joint together by a flexible linker peptide ((G4S) 4, SEQ ID No. 7) and separated from the HA tag by means of another linker peptide (G4S, SEQ ID No. 11). The nucleotide sequence encoding the human anti DEC205 scFV was optimized and chemically synthesized by Eurofins genomics according to what is described in Birkholz K et al, Blood 2010 and inserted between the sequences encoding the fourth and fifth amino acids of the mature pIII protein.

variable light chain of the monoclonal antibody
anti DEC205-Nucleotide sequence
(SEQ ID No. 2)
GCGGCTCAACCGGCGATGGCCGATTACAAGCAAGCGGTGGTAACCCAGGA

ATCCGCACTGACGACCTCGCCAGGGGAAACCGTGACACTGACTTGTCGCT

CGTCTACAGGAGCCGTTACCATTTCCAACTATGCCAATTGGGTACAGGAG

AAACCGGACCATCTGTTTACGGGCTTAATTGGCGGGATCAACAATCGCGC

TCCTGGCGTTCCAGCGCGTTTTAGCGGTAGCTTGATTGGCGATAAAGCCG

CTCTTACCATTACTGGTGCACAGACCGAGGATGAAGCCATCTACTTTTGC

GCACTGTGGTATAACAACCAGTTTATCTTCGGTAGCGGCACCAAAGTCAC

GGTCTTG variable light chain of the monoclonal antibody
anti DEC205-Amino acid sequence
(SEQ ID No. 3)
AAQPAMADYKQAVVTQESALTTSPGETVTLTCRSSTGAVTISNYANWVQE

KPDHLFTGLIGGINNRAPGVPARFSGSLIGDKAALTITGAQTEDEAIYFC

ALWYNNQFIFGSGTKVTVL variable heavy chain of the monoclonal antibody
anti DEC205-Nucleotide sequence
(SEQ ID No. 4)
GAAGTCCAGTTACAGCAAAGTGGCCCGGTTCTGGTGAAACCGGGAGCGAG

TGTGAAGATGTCGTGCAAAGCCTCTGGAAACACCTTTACTGACTCGTTTA

TGCACTGGATGAAACAGTCGCATGGCAAATCACTGGAATGGATTGGTATC

ATCAACCCGTACAATGGCGGGACCTCTTACAACCAGAAGTTCAAGGGCAA

AGCGACCCTGACTGTGGATAAATCCAGCAGCACGGCGTATATGGAGCTCA

ACAGCCTGACCAGTGAGGATAGCGCCGTATATTATTGCGCTCGCAATGGG

GTACGCTACTATTTCGACTATTGGGGCCAGGGTACGACGTTGACCGTTTC

ATCTGCCTCAGGGGCG variable heavy chain of the monoclonal antibody
anti DEC205-Amino acid sequence
(SEQ ID No. 5)
EVQLQQSGPVLVKPGASVKMSCKASGNTFTDSFMHWMKQSHGKSLEWIGI

INPYNGGTSYNQKFKGKATLTVDKSSSTAYMELNSLTSEDSAVYYCARNG

VRYYFDYWGQGTTLTVSSASGA flexible peptide linker ((G4S)4)-Nucleotide sequence
(SEQ ID No. 6)
GGTGGAGGCGGTGGTAGTGGCGGCGGTGGGTCCGGCGGTGGCGGTAGTGG

CGGTGGTGGTTCT flexible peptide linker ((G4S)4)-Amino acid sequence
(SEQ ID No. 7)
GGGGSGGGGSGGGGSGGGGS HA tag-Nucleotide sequence
(SEQ ID No. 8)
ACCTCCGGTTACCCGTACGACGTTCCGGACTACGCT HAtag-Amino acid sequence
(SEQ ID No. 9)
TSGYPYDVPDYA linker peptide (G4S)-Nucleotide sequence
(SEQ ID No. 10)
GGTGGTGGTGGTTCTGGTGGTGGTGGT linker peptide (G4S)-Nucleotide sequence
(SEQ ID No. 11)
GGGGSGGGG fdXCL1

The sequence encoding the chemokine XCL1 was inserted between the sequences encoding the fourth and fifth amino acids of the mature pIII protein and is separated from the HA tag by a sequence encoding the linker peptide (G4S, SEQ ID No. 11)

Nucleotide and Amino Acid Sequence of pIII,
Modified for the Insertion of Two Unique XhoI and
SpeI Restriction Sites Nucleotide sequence of pIII (SEQ ID No. 12)

GTGAAAAAATTATTATTCGCAATTCCTTTAGTTGTTCCTTTCTATTCTCACTCgagTGAAACTGTTactAGTTGTTTAGC

AAAACCTCATACAGAAAATTCATTTACTAACGTCTGGAAAGACGACAAAACTTTAGATCGTTACGCTAACTATGAGGGCT

GTCTGTGGAATGCTACAGGCGTTGTGGTTTGTACTGGTGACGAAACTCAGTGTTACGGTACATGGGTTCCTATTGGGCTT

GCTATCCCTGAAAATGAGGGTGGTGGCTCTGAGGGTGGCGGTTCTGAGGGTGGCGGTTCTGAGGGTGGCGGTACTAAACC

TCCTGAGTACGGTGATACACCTATTCCGGGCTATACTTATATCAACCCTCTCGACGGCACTTATCCGCCTGGTACTGAGC

AAAACCCCGCTAATCCTAATCCTTCTCTTGAGGAGTCTCAGCCTCTTAATACTTTCATGTTTCAGAATAATAGGTTCCGA

AATAGGCAGGGTGCATTAACTGTTTATACGGGCACTGTTACTCAAGGCACTGACCCCGTTAAAACTTATTACCAGTACAC

TCCTGTATCATCAAAAGCCATGTATGACGCTTACTGGAACGGTAAATTCAGAGACTGCGCTTTCCATTCTGGCTTTAATG

AGGATCCATTCGTTTGTGAATATCAAGGCCAATCGTCTGACCTGCCTCAACCTCCTGTCAATGCTGGCGGCGGCTCTGGT

GGTGGTTCTGGTGGCGGCTCTGAGGGTGGCGGCTCTGAGGGTGGCGGTTCTGAGGGTGGCGGCTCTGAGGGTGGCGGTTC

CGGTGGCGGCTCCGGTTCCGGTGATTTTGATTATGAAAAAATGGCAAACGCTAATAAGGGGGCTATGACCGAAAATGCCG

ATGAAAACGCGCTACAGTCTGACGCTAAAGGCAAACTTGATTCTGTCGCTACTGATTACGGTGCTGCTATCGATGGTTTC

ATTGGTGACGTTTCCGGCCTTGCTAATGGTAATGGTGCTACTGGTGATTTTGCTGGCTCTAATTCCCAAATGGCTCAAGT

CGGTGACGGTGATAATTCACCTTTAATGAATAATTTCCGTCAATATTTACCTTCTTTGCCTCAGTCGGTTGAATGTCGCC

CTTATGTCTTTGGCGCTGGTAAACCATATGAATTTTCTATTGATTGTGACAAAATAAACTTATTCCGTGGTGTCTTTGCG

TTTCTTTTATATGTTGCCACCTTTATGTATGTATTTTCGACGTTTGCTAACATACTGCGTAATAAGGAGTCTTAA

Amino acid sequence of pIII (SEQ ID No. 13)

VKKLLFAIPLVVPFYSHSSETVTSCLAKPHTENSFTNVWKDDKTLDRYANYEGCLWNATGVVVCTGDETQCYGTWVPIGL

AlPENEGGGSEGGGSEGGGSEGGGTKPPEYGDTPIPGYTYINPLDGTYPPGTEQNPANPNPSLEESQPLNTFMFQNNRFR

NRQGALTVYTGTVTQGTDPVKTYYQYTPVSSKAMYDAYWNGKFRDCAFHSGFNEDPFVCEYQGQSSDLPQPPVNAGGGSG

GGSGGGSEGGGSEGGGSEGGGSGGGSGSGDFDYEKMANANKGAMTENADENALQSDAKGKLDSVATDYGAAIDGF

IGDVSGLANGNGATGDFAGSNSQMAQVGDGDNSPLMNNFRQYLPSLPQSVECRPYVFGAGKPYEFSIDCDKINLFRGVFA

FLLYVATFMYVFSTFANILRNKES

Nucleotide and amino acid sequence of pIII in fdAMPLAY388-HA, modified for
the insertion of an HA tag peptide and a unique KpnI restriction site
Nucleotide sequence of pIII in fdAMPLAY388-HA (SEQ ID No. 14)

GTGAAAAAATTATTATTCGCAATTCCTTTAGTTGTTCCTTTCTATTCTCActcgagTGAAACTGTTACTAGTggtaccTC CGGTTACCCGTACGACGTTCCGGACTACGCTactAGTTGTTTAGCAAAACCTCATACAGAAAATTCATTTACTAACGTCT GGAAAGACGACAAAACTTTAGATcgttacgctaactatgagggcTGTCTGTGGAATGCTACAGGCGTTGTGGTTTGTACT

GGTGACGAAACTCAGTGTTACGGTACATGGGTTCCTATTGGGCTTGCTATCCCTGAAAATGAGGGTGGTGGCTCTGAGGG

TGGCGGTTCTGAGGGTGGCGGTTCTGAGGGTGGCGGTACTAAACCTCCTGAGTACGGTGATACACCTATTCCGGGCTATA

CTTATATCAACCCTCTCGACGGCACTTATCCGCCTGGTACTGAGCAAAACCCCGCTAATCCTAATCCTTCTCTTGAGGAG

TCTCAGCCTCTTAATACTTTCATGTTTCAGAATAATAGGTTCCGAAATAGGCAGGGTGCATTAACTGTTTATACGGGCAC

TGTTACTCAAGGCACTGACCCCGTTAAAACTTATTACCAGTACACTCCTGTATCATCAAAAGCCATGTATGACGCTTACT

GGAACGGTAAATTCAGAGACTGCGCTTTCCATTCTGGCTTTAATGAGGATCCATTCGTTTGTGAATATCAAGGCCAATCG

TCTGACCTGCCTCAACCTCCTGTCAATGCTGGCGGCGGCTCTGGTGGTGGTTCTGGTGGCGGCTCTGAGGGTGGCGGCTC

TGAGGGTGGCGGTTCTGAGGGTGGCGGCTCTGAGGGTGGCGGTTCCGGTGGCGGCTCCGGTTCCGGTGATTTTGATTATG

AAAAAATGGCAAACGCTAATAAGGGGGCTATGACCGAAAATGCCGATGAAAACGCGCTACAGTCTGACGCTAAAGGCAAA

-continued

```
CTTGATTCTGTCGCTACTGATTACGGTGCTGCTATCGATGGTTTCATTGGTGACGTTTCCGGCCTTGCTAATGGTAATGG

TGCTACTGGTGATTTTGCTGGCTCTAATTCCCAAATGGCTCAAGTCGGTGACGGTGATAATTCACCTTTAATGAATAATT

TCCGTCAATATTTACCTTCTTTGCCTCAGTCGGTTGAATGTCGCCCTTATGTCTTTGGCGCTGGTAAACCATATGAATTT

TCTATTGATTGTGACAAAATAAACTTATTCCGTGGTGTCTTTGCGTTTCTTTTATATGTTGCCACCTTTATGTATGTATT

TTCGACGTTTGCTAACATACTGCGTAATAAGGAGTCTTAA
```

Amino acid sequence of pIII in fdAMPLAY388-HA
(SEQ ID No. 15)

```
VKKLLFAIPLVVPFYSHSSETVTSGTSGYPYDVPDYATSCLAKPHTENSFTNVWKDDKTLDRYANYEGCLWNATGVVVCT

GDETQCYGTWVPIGLAIPENEGGGSEGGGSEGGGSEGGGTKPPEYGDTPIPGYTYINPLDGTYPPGTEQNPANPNPSLEE

SQPLNTFMFQNNRFRNRQGALTVYTGTVTQGTDPVKTYYQYTPVSSKAMYDAYWNGKFRDCAFHSGFNEDPFVCEYQGQS

SDLPQPPVNAGGGSGGGSGGGSEGGGSEGGGSEGGGSEGGGSGGGSGSGDFDYEKMANANKGAMTENADENALQSDAKGK

LDSVATDYGAAIDGFIGDVSGLANGNGATGDFAGSNSQMAQVGDGDNSPLMNNFRQYLPSLPQSVECRPYVFGAGKPYEF

SIDCDKINLFRGVFAFLLYVATFMYVFSTFANILRNKES
```

Nucleotide and amino acid sequence of pVIII, modified for the insertion of two unique SacII and StyI restriction sites
Nucleotide sequence of pVIII
(SEQ ID No. 16)

```
ATGAAAAAGTCTTTAGTCCTCAAAGCCTCCGTAGCCGTTGCTACCCTCGTTCCGATGCTGTCTTTCGCCGCGGAGGgTgA

CgatCCcGCcAAgGCGGCCTTTGACTCCCTGCAAGCCTCAGCGACCGAATATATCGGTTATGCGTGGGCGATGGTTGTTG

TCATTGTCGGCGCAACTATCGGTATCAAGCTGTTTAAGAAATTCACCTCGAAAGCAAGCTGA
```

Amino acid sequence of pVIII
(SEQ ID No. 17)

```
MKKSLVLKASVAVATLVPMLSFAAEGDDPAKAAFDSLQASATEYIGYAWAMVVVIVGATIGIKLFKKFTSKAS
```

XCL1 chemokine-Nucleotide sequence
(SEQ ID No. 18)

```
GGGTCAGAAGTGTCCGACAAACGCACATGCGTGTCTCTGACGACCCAACGCTTACCGGTTTCGCGCATTAAGACGTATAC

CATTACCGAGGGTAGTTTGCGTGCTGTCATCTTTATCACCAAACGTGGCCTGAAAGTGTGTGCAGATCCGCAAGCGACAT

GGGTTCGCGATGTAGTCCGTAGCATGGATCGCAAAAGCAATACCCGGAACAACATGATTCAGACGAAACCAACCGGTACT

CAGCAGTCGACGAATACTGCCGTAACCCTGACTGGC
```

XCL1 chemokine-Amino acid sequence
(SEQ ID No. 19)

```
GSEVSDKRTCVSLTTQRLPVSRIKTYTITEGSLRAVIFITKRGLKVCADPQATWVRDVVRSMDRKSNTRNNMIQTKPTGTQ

QSTNTAVTLTG
```

HA tag-Nucleotide sequence
(SEQ ID No. 8)

```
ACCTCCGGTTACCCGTACGACGTTCCGGACTACGCT
```

HA tag-Amino acid sequence
(SEQ ID No. 9)

```
TSGYPYDVPDYA
``` linker peptide (G4S)-Nucleotide sequence
(SEQ ID No. 10)

```
GGTGGTGGTGGTTCTGGTGGTGGTGGT
``` linker peptide (G4S)-Amino acid sequence
(SEQ ID No. 11)

```
GGGGSGGGG
```

The DNA sequences encoding the human anti-DEC205 scFv and the XCL1 chemokine were chemically optimized and synthesized by Eurofins Genomics and cloned in the genome of the fdAMPLAY388-HA bacteriophage described above (Sartorius R et al., 2011) previously digested with the XhoI (R0146S, New England Biolabs)-KpnI (R0142S, New England Biolabs) restriction enzymes to obtain the fda-hDEC and fdXCL1 bacteriophage vectors expressing the sequences of interest (a-hDEC and XCL1) between the fourth and fifth amino acids of the mature pIII protein.

To purify the phage preparations used, the virions were precipitated by the supernatant of E. coli cultures with PEG6000/NaCl (Sigma), purified by cesium chloride gradient ultracentrifugation and subjected to removal of the bacterial lipopolysaccharide by extraction with Triton X114 (Sigma). The expression of the recombinant proteins as a fusion to pIII protein on purified virions was assessed by acrylamide gel electrophoretic run in the presence of sodium dodecyl sulfate (SDS-PAGE) and by western blot analysis using a mouse anti-HA tag monoclonal antibody (code 12CA5, Roche).

Conjugation of Bacteriophage Particles to FITC

In order to conjugate fda-hDEC, fdXCL1 or fdWT with the isomer I of fluorescein isothiocyanate (FITC) (F7250, Sigma-Aldrich), 10 mg/ml of a solution of each bacteriophage in PBS were dialysed against carbonate buffer (31 mm Na2CO3, 31 mM NaHCO3, pH 9.4) 1:20 in PBS, at 4° C. The solution was substituted with the same buffer containing 0.07 mg/ml of fluorescein isothiocyanate for 48 hours at 4° C. Finally, the samples were dialysed against PBS1X until the assorbance at 495 nm of the dialysis solution was zero.

Internalization of Phage Particles by Subpopulations of Dendritic Cells

Human dendritic cells (DCs) belonging to the myeloid and plasmacytoid subtypes were isolated from mononucleated cells of the peripheral blood obtained from healthy volunteer donors by Ficoll gradient centrifugation and subsequent magnetic selection using the Miltenyi Biotec Pan DC Enrichment Kit (code 130-100-777).

The purified human DCs were then incubated with the phages conjugated with FITC fda-hDEC, fdXCL1 or fd WT (100 micrograms/ml) for 15 minutes at 37 degrees, the cells were then transferred at 4 degrees, washed 3 times with cold PBS, stained with anti-CD1C-PE (Biolegend, 331506), anti-CD303PE/Cy7 (Biolegend 354.214) and anti-CD141-APC (Biolegend 344.106) antibodies, and analysed by flow cytometry.

EXAMPLES

Example 1

The authors of the present invention tested the ability of aGalCer loaded on phage particles to be presented by dendritic cells derived from mouse bone marrow, and to activate in vitro iNKT cells. BMDCs were incubated with different doses of free aGalCer or aGalCer loaded on bacteriophage particles. After washing, the DCs were cultured with the FF13 iNKT hybridoma cell line. As shown in FIG. 1, the aGalCer vehiculated by the bacteriophage was presented by BMDCs, triggering the activation of the iNKT hybridoma, as ascertained by IL-2 production.

Example 2

Figure 2:
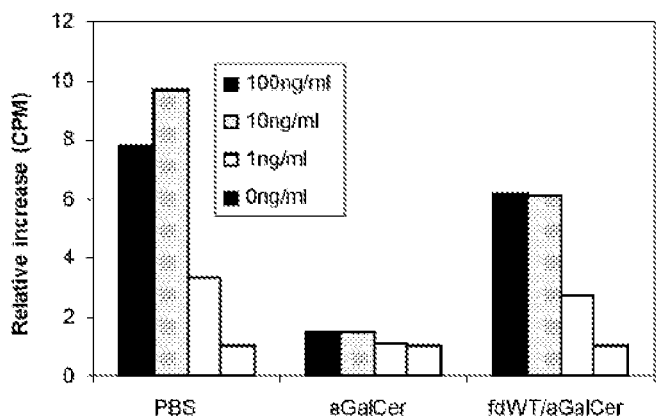
FIG. 2: The figure shows the response to aGalCer by splenocytes isolated from mice previously immunized with aGalCer. The experimental animals received an administration of soluble aGalCer (aGalCer) or conjugated to phage particles (fdWT/aGalCer). After 24 hours, the animals were sacrificed and the isolated splenocytes were cultured with scalar doses of soluble aGalCer (0, 1, 10, 100 ng/ml). After 3 days in culture, the proliferative capacity of cultured cells was assessed by tritiated thymidine incorporation assay. Cpm (counts per minute) (A). Furthermore, the amount of IL-2 released in culture supernatants was assessed by ELISA (B).
Figure 2:
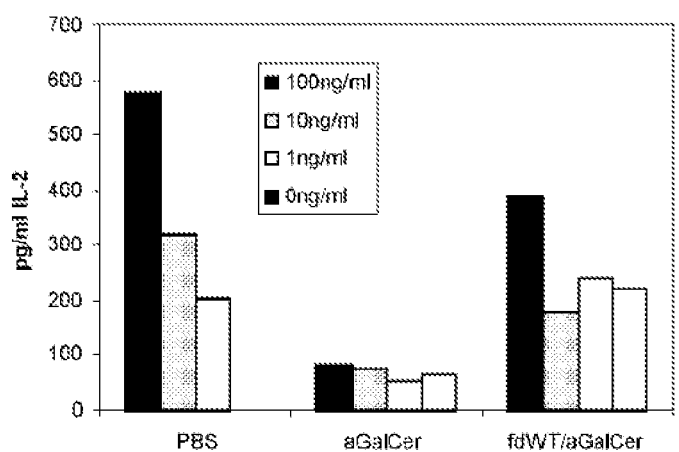

It is known that the soluble aGalCer, administered intravenously to mice, leads to a decrease in the levels of T-cell receptor (TCR) on iNKTs, and that the splenocytes of mice injected with soluble aGalCer, compared to naive splenocytes, lose rapidly their ability to proliferate and produce cytokines after in vitro restimulation with the aGalCer itself. On the other hand, the authors of the present invention have observed that the splenocytes of mice injected with aGalCer bacteriophages are still able to respond in vitro to the administration of a recall with soluble aGalCer, being able to proliferate and produce IL-2 in response to restimulation with aGalCer (FIG. 2 A, B).

Example 3

Figure 3:
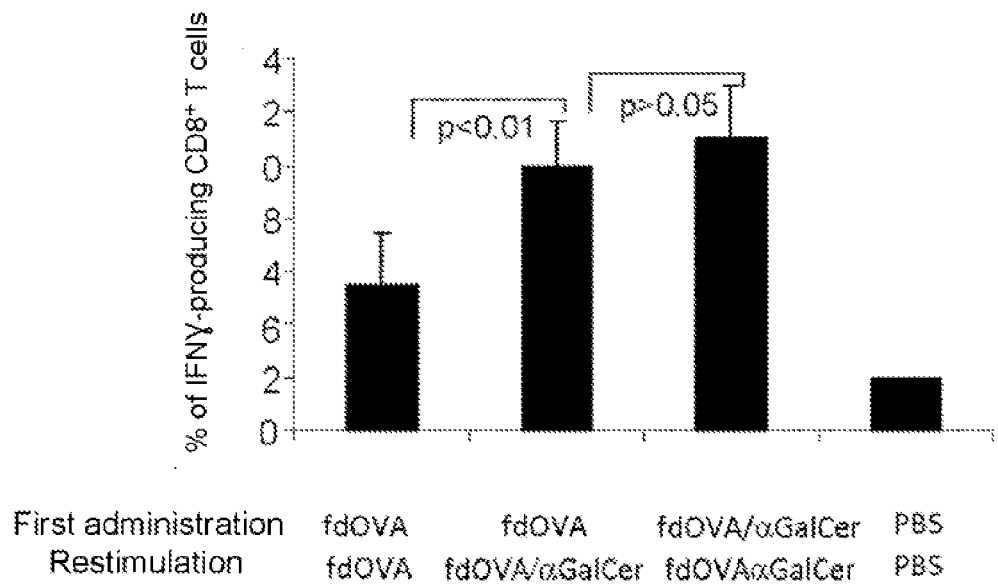
FIG. 3: Groups of mice (n=5) were immunized at day 0 (before administration) and at day 14 (restimulation) with phage particles vehiculating the SIINFEKL (fdOVA) peptide, whether conjugated with aGalCer as indicated on the axis of abscissas. Control animals were inoculated with PBS. At day 21, the splenocytes were isolated and the percentage of OVA peptide-specific CD8+ cells able to produce gamma interferon (IFN$\gamma$) (A) was analysed. Furthermore, Kb-OVA (B) dextramer staining determined the frequency of CD8+ cells able to recognize the OVA (SIINKFEL) peptide.
Figure 3:
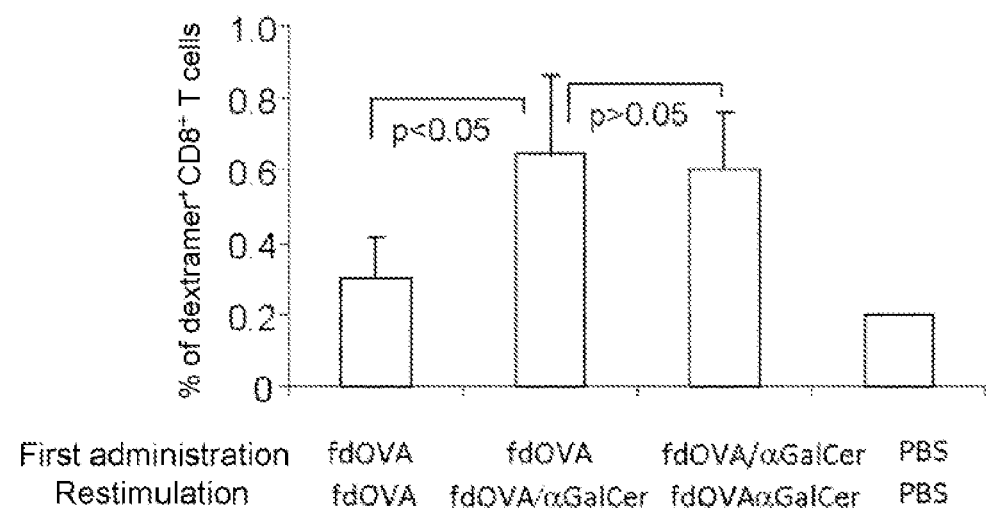

The authors then studied the impact on the induction of adaptive immune responses of the simultaneous vehiculation of aGalCer and of an antigen simultaneously expressed on the bacteriophage scaffold. They demonstrated that the co-vehiculation of the model antigenic peptide (OVA SIINFEKL) and of the aGalCer further enhances the CD8+ T cell-mediated antigen-specific immune response. In fact, two administrations of fdOVA/aGalCer in mice are able to induce a higher percentage of OVA-specific CD8+ T cells producing IFN-g, compared to mice inoculated twice only with fdOVA (FIG. 3 A, B). The frequency of OVA-specific $CD8^+$ T cells in the spleen was assessed by the cytofluorimeter 21 days after the first administration of bacteriophages, using the anti-CD8 antibody and SIINFEKL-pentamer staining, and the IFN-g production was measured by intracellular staining on CD8+ cells.

The results were similar in a group of mice that received priming with fdOVA and the recall with fdOVA/aGalCer, which indicates that the adjuvant effect of administration of aGalCer via bacteriophage particles can be observed even after a single administration.

Example 4

Figure 4:
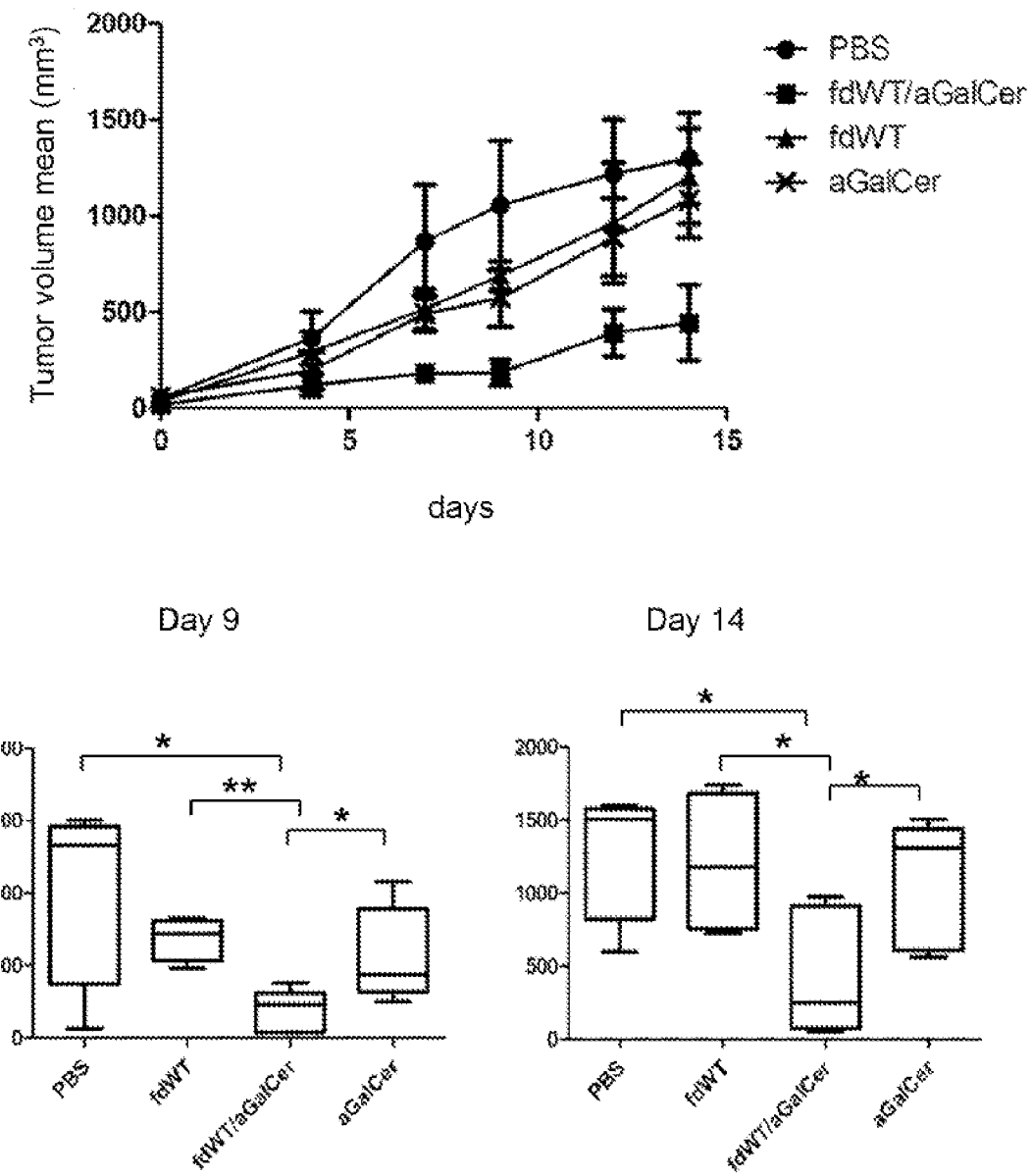
FIG. 4: Therapeutic vaccination with fdWT/aGalCer inhibits tumour growth. (A) Tumour cells of the B16 melanoma line were administered in the side of C57BL6 mice (n=5 per group). When the tumour was palpable, the animals were immunized with intratumoural administration of PBS (circles); of 2.5 micrograms of soluble aGalCer (crosses), 50 micrograms of fdWT bacteriophages (triangles); or 50 micrograms of fdWT/aGalCer (squares). The figure shows the average tumour size in each group of animals. The curves were interrupted when the animals were sacrificed, since the tumours had reached the diameters of 1.500 mm$^3$. (B) Box plot of the tumour size at day 9 and 14. P<0.05 is marked with an asterisk (*), P<0.01 is marked with two asterisks (**) (Student t-test).

The authors of the present invention tested the antitumour effect of the aGalCer vehiculated by bacteriophage particles in mice implanted with a melanoma cell line. The authors injected subcutaneously B16 melanoma cells into C57BL/6 mice, and when the tumours became palpable, the mice were intratumourally treated with soluble aGalCer, fd bacteriophage or fdWT/aGalCer. The authors observed that the administration of free aGalCer was not able to protect animals from tumour growth, whereas aGalCer vehiculated by bacteriophage particles led to a significant delay in tumour growth and a higher survival (FIG. 4).

Example 5

Figure 5:
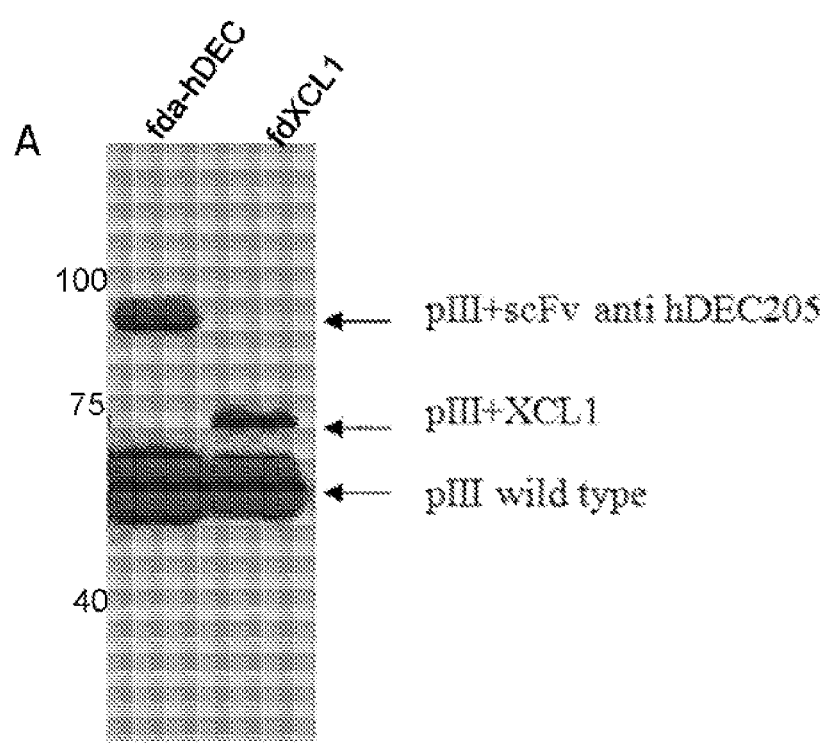
FIG. 5: (A) Western blot analysis of phage particles able to be vehiculated to human dendritic cells and expressing the anti-DEC205 antibody fragment (fda-hDEC, line 1) or the XCL1 chemokine (fdXCL1, line 2) as a fusion to pIII protein. The pIII protein was detected using a monoclonal anti-HA antibody. Arrows indicate wild type pIII, pIII+ScFv or pIII+XCL1. (B) DC isolated from donors were incubated for 15 minutes with fdWT phage particles (fdWT, Blank), or expressing XCL1 chemokine (fdXCL1, grey) or expressing the anti-DEC-205 antibody fragment (fda-hDEC, black) pre-conjugated with fluorescein isothiocyanate (FITC). The dendritic cells were then analysed using anti-CD1c, anti-CD141 and anti-CD303 antibodies by flow cytometry.
Figure 5:
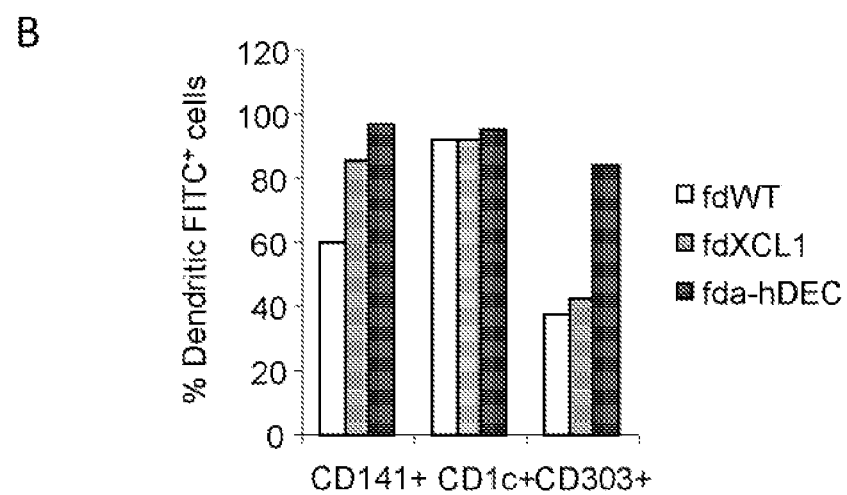

The authors designed two new formulations based on filamentous bacteriophages expressing on their surface, as a fusion with the pIII protein, a scFv which recognizes the human DEC-205 receptor, or the XCL1 chemokine binding the human XCR1 receptor, referred to as fda-hDEC and fdXCL1, respectively. As shown in FIG. 5A, a fusion protein of 88 kDa (predicted combined molecular mass of the pIII-protein fused to the anti-DEC-205 scFv) is expressed by the fda-hDEC, and a fusion protein of 73 kDa (predicted combined molecular mass of pIII protein fused to XCL1) is expressed by fdXCL1. A band corresponding to the native pIII is expressed in all the preparations. The authors then compared the levels of internalization of the human anti-DEC-205 phage particles (fda-hDEC), XCL1 (fdXCL1) or fdWT bacteriophages using phage preparations conjugated with the FITC fluorescent molecule and dendritic cells isolated from human blood. An improvement in the internalization of fda-hDEC particles after 15 minutes of incubation has been demonstrated in all human DC subpopulations expressing DEC 205, whereas only $CD141^+$ $XCR1^+$ DCs show an increase in the internalization of fdXCL1 particles, compared to fdWT phages (FIG. 5b).

REFERENCES

1. De Libero G and Mori L. *Trends in Immunology* 2012, 33:103-111
2. Sullivan B A and Kronenberg M. *J Clin Invest* 2005, 115: 570-82
3. Thapa P, Zhang G, Xia C et al. *Vaccine* 2009, 26: 3484-8

4. Sartorius R, D'Apice L, Trovato M et al. *Embo Mol Med* 2015, 17:973-88
5. Sehgal K, Ragheb R, Fahmy T M et al J Immunol 2014, 193:2297-305
6. Sartorius R et al. *Eur J Immunol.* 2011 September; 41 (9):2573-84
7. Lutz M. et al. *J. Immunol. Methods* 1999. 223: 77-92
8. Schümann J et al. *Eur J Immunol.* 2007 June; 37 (6):1431-41.)
9. Kay, B., Winter, J. and McCafferty, J. Phage Display of Peptides and Proteins: A Laboratory Manual. Academic Press, 1996.
10. Berdichevsky, Y., et al., J. Immunol. Methods 228, 151-62, 1999.
11. Benhar, I. and Reiter, Y. Phage display of single-chain antibodies. In: J. Colligan (Ed) Current Protocols in Immunology, Vol. 10.19B. John Wiley & Sons, Inc, USA, 2001.
12. Benhar, I. Biotechnology Advances 19, 1-33, 2001.
13. Sambrook, J., Russell, D. W. and Maniatis, T. Molecular cloning: A laboratory manual. Cold Spring Harbor Laboratory, Cold Spring Harbor, N.Y., 1989.
14. Saggio, I., Gloaguen, I. and Laufer, R. Gene 152, 35-39, 1995.
15. Uppala, A. et al., Comb. Chem. High Throughput Screen. 3, 373-392, 2000.
16. Sternberg, N. and Hoess, R. H. Proc. Natl. Acad. Sci. (USA) 92, 1609-13, 1995.
17. Mikawa, Y. G., Maruyama, I. N. and Brenner, S. J. Mol. Biol. 262, 21-30, 1996.
18. Maruyama, I. N., et al., Proc. Natl. Acad. Sci. (USA) 91, 8273-8277, 1994.
19. Lee, C. S. and Guo, P. J. Virol. 69, 5018-23, 1995.
20. Hong, Y. R. and Black, L. W. Gene 136, 193-8, 1993.
21. Heal, K. G., et al., Vaccine 18, 251-8, 1999.
22. Efimov, V. P., Nepluev, I. V. and Mesyanzhinov, V. V. Virus Genes 10, 173-7, 1995.
23. Ren, Z. and Black, L. W. Gene 215, 439-44, 1998.
24. Carbonell, X. and Villaverde, A. Gene 176, 225-9, 1996.
25. Brent, R., et al., Current Protocols in Molecular Biology. John Wiley & Sons Inc., 2003.
26. Borrebaeck, C. A. K. Antibody Engineering (Breakthroughs in Molecular Biology). Oxford University Press, 1995.
27. Lo, B. K. C. Antibody Engineering: Methods and Protocols (Methods in Molecular Biology). Humana Press, 2003.
28. Becerril, B. et al., Biophys. Res. Commun. 255,386-93, 1999.
29. Kassner, P. D. et al., Biochem. Biophys. Res. Commun. 264, 921-8, 1999.
30. Poul, M. A. and Marks, J. D. J. Mol. Biol. 288, 203-11, 1999.
31. Larocca, D. and Baird, A. Drug Disc. Today 6, 793-801, 2001.
32. Larocca, D., Jensen-Pergakes, K., Burg, M. A. and Baird, A. Mol. Therap. 3, 2001.
33. Urbanelli, L., et al., Mol. Biol. 313, 965-976, 2001.
34. Remington's Pharmaceutical Sciences, 15th Ed. Easton: Mack Publishing Co. pp 1405-1412 and 1461-1487, 1975.
35. Goodman and Gilman, The Pharmacological Basis of Therapeutics, Eighth Edition, McGraw-Hill, Inc. (Health Professions Division), 1990.
36. Ausubel, R. M. et al., eds. "Current Protocols in Molecular Biology," Volumes I-III, John Wiley & Sons, Baltimore, Md., 1994.
37. Malik, P. & Perham, R. N. Gene 171, 49-51, 1996.
38. Zanoni I et al. Science 352:6290, 2016.
39. Zajonc and Girardi Frontiers in Immunology 6:400, 2015.
40. De Libero G and Mori L Nature Reviews Immunology 5,485-496, 2005.
41. Birkholz K et al, Blood. 2010 116 (13):2277-85.

---

The invention claimed is:

1. A pharmaceutical composition comprising lipid-bacteriophage conjugates, wherein the bacteriophage is conjugated to at least one lipid by means of a non-covalent bond and the bacteriophage lipid ratio is between 3:1 and 100:1; wherein the lipid is selected from the group consisting of alpha-galactosylceramide (aGalCer), glycosphingolipids, palmitoyl-2-arachidonoyl-sn-glycero-3-phosphocholine (PAPC), monophosphoryl lipid A and their natural or synthetic analogues and the bacteriophage is a filamentous bacteriophage.

2. The pharmaceutical composition according to claim 1 wherein the immunologically active lipid is aGalCer.

3. The pharmaceutical composition according to claim 1 wherein the bacteriophage is a filamentous bacteriophage engineered to express an exogenous sequence or a fragment thereof, and said exogenous sequence or a fragment thereof stimulates an immune response and/or selectively binds to a cell surface molecule on a target cell.

4. The pharmaceutical composition according to claim 3, wherein the exogenous sequence or a fragment thereof is encoded by a nucleic acid fused to a nucleotide sequence encoding a coat protein of the bacteriophage.

5. The pharmaceutical composition according to claim 4, wherein the exogenous sequence encodes a protein or a fragment thereof, an antibody or a fragment thereof, or a chemokine.

6. The pharmaceutical composition according to claim 5, wherein the protein is ovalbumin, the antibody or antibody fragment is a single chain antibody fragment (scFv) directed against the DEC 205 receptor comprising a variable region of a light chain having an amino acid sequence of SEQ ID NO: 3 and a variable region of a heavy chain having an amino acid sequence of SEQ ID NO: 5 and the chemokine is XCL1.

7. The pharmaceutical composition according to claim 4, wherein the coat protein is the protein pIII or the protein pVIII.

8. The pharmaceutical composition according to claim 4, wherein the coat protein has an amino acid sequence selected from the group consisting of: SEQ ID NO: 13, SEQ ID NO: 15 and SEQ ID NO: 17.

9. The pharmaceutical composition according to claim 3, wherein the target cell is a dendritic cell.

10. The pharmaceutical composition according to claim 1 wherein the bacteriophage is linked to a combination of lipids.

11. The pharmaceutical composition according to claim 1, wherein the filamentous bacteriophage is selected from the group consisting of: m13, fd and f1.

12. The pharmaceutical composition according to claim 1 further comprising pharmaceutically acceptable excipients, vehicles or diluents.

13. A method for the treatment of an infection or an hyperproliferative disease, comprising administering a pharmaceutical composition of claim 1 to a subject in need thereof.

14. The method according to claim 13 wherein the hyperproliferative disease is a tumour.

15. The pharmaceutical composition according to claim 9, wherein said dendritric cell is a myeloid dendritric cell type I or type II, or a plasmacytoid dendritic cell.

16. The method of claim 14, wherein the tumour is a melanoma.

* * * * *

UNITED STATES PATENT AND TRADEMARK OFFICE
CERTIFICATE OF CORRECTION

| | |
|---|---|
| PATENT NO. | : 11,744,901 B2 |
| APPLICATION NO. | : 16/478338 |
| DATED | : September 5, 2023 |
| INVENTOR(S) | : Piergiuseppe De Berardinis and Rossella Sartorius |

It is certified that error appears in the above-identified patent and that said Letters Patent is hereby corrected as shown below:

On the Title Page

In Column 1, item (71) Applicant should read:
--CONSIGLIO NAZIONALE DELLE RICERCHE,
Rome (IT)--

In the Claims

In Column 39, Line 13, Claim 1 should read:
--1. A pharmaceutical composition comprising lipid-bacteriophage conjugates, wherein the bacteriophage is conjugated to at least one lipid by means of a non-covalent bond and the bacteriophage:lipid ratio is between 3:1 and 100:1; wherein the lipid is selected from the group consisting of alpha-galactosylceramide (aGalCer), glycosphingolipids, palmitoyl-2-arachidonoyl-sn-glycero-3-phosphocholine (PAPC), monophosphoryl lipid A and their natural or synthetic analogues and the bacteriophage is a filamentous bacteriophage.--

Signed and Sealed this
Thirteenth Day of February, 2024

Katherine Kelly Vidal
*Director of the United States Patent and Trademark Office*